(12) United States Patent
Ito et al.

(10) Patent No.: US 11,633,523 B2
(45) Date of Patent: Apr. 25, 2023

(54) METHOD FOR PRODUCING CELL TISSUE, AND POROUS FILM

(71) Applicant: FUJIFILM CORPORATION, Tokyo (JP)

(72) Inventors: Koju Ito, Kanagawa (JP); Shun Goto, Kanagawa (JP); Souichi Kohashi, Kanagawa (JP); Kohji Nakazawa, Fukuoka (JP); Hiroshi Yabu, Miyagi (JP)

(73) Assignee: FUJIFILM CORPORATION, Tokyo (JP)

( * ) Notice: Subject to any disclaimer, the term of this patent is extended or adjusted under 35 U.S.C. 154(b) by 690 days.

(21) Appl. No.: 16/294,931

(22) Filed: Mar. 7, 2019

(65) Prior Publication Data
US 2019/0201585 A1    Jul. 4, 2019

Related U.S. Application Data

(63) Continuation of application No. PCT/JP2017/033605, filed on Sep. 15, 2017.

(30) Foreign Application Priority Data

Sep. 27, 2016  (JP) .............................. JP2016-188627

(51) Int. Cl.
| | | |
|---|---|---|
| *C12N 5/00* | (2006.01) | |
| *A61L 27/56* | (2006.01) | |
| *C12N 5/0775* | (2010.01) | |
| *C12N 5/078* | (2010.01) | |
| *C12N 5/071* | (2010.01) | |
| *C12N 5/077* | (2010.01) | |
| *C12M 1/12* | (2006.01) | |
| *C12M 1/42* | (2006.01) | |
| *C08J 9/28* | (2006.01) | |
| *C12M 3/00* | (2006.01) | |

(52) U.S. Cl.
CPC ................. *A61L 27/56* (2013.01); *C08J 9/28* (2013.01); *C12M 21/08* (2013.01); *C12M 25/00* (2013.01); *C12M 35/08* (2013.01); *C12N 5/0068* (2013.01); *C12N 5/069* (2013.01); *C12N 5/0651* (2013.01); *C12N 5/0656* (2013.01); *C12N 5/0663* (2013.01)

(58) Field of Classification Search
None
See application file for complete search history.

(56) References Cited

U.S. PATENT DOCUMENTS

| | | | | |
|---|---|---|---|---|
| 6,479,064 B1 * | 11/2002 | Atala | .................. | A61P 13/12 424/423 |
| 2002/0155594 A1 | 10/2002 | Hsieh et al. | | |
| 2006/0127368 A1 | 6/2006 | Miwa et al. | | |
| 2008/0215073 A1 | 9/2008 | Iwanaga et al. | | |
| 2009/0041825 A1 | 2/2009 | Kotov et al. | | |
| 2010/0171231 A1 | 7/2010 | Shimomura et al. | | |
| 2010/0273667 A1 * | 10/2010 | Kotov | .................... | C12M 21/08 422/135 |
| 2016/0298087 A1 * | 10/2016 | Qu | ....................... | C12N 5/0671 |

FOREIGN PATENT DOCUMENTS

| | | |
|---|---|---|
| EP | 1961809 A1 | 8/2008 |
| JP | H06-284883 A | 10/1994 |
| JP | 2001-523483 A | 11/2001 |
| JP | 2004-216119 A | 8/2004 |
| JP | 2005-110709 A | 4/2005 |
| JP | 2007-291367 A | 11/2007 |
| JP | 2008-199962 A | 9/2008 |
| JP | 2008-307180 A | 12/2008 |
| JP | 2009-213421 A | 9/2009 |
| JP | 2009-254271 A | 11/2009 |
| JP | 2009-273444 A | 11/2009 |
| JP | 4437227 B2 | 3/2010 |
| JP | 2012-006010 A | 1/2012 |
| WO | 2006/093207 A1 | 9/2006 |
| WO | 2007094929 A2 | 8/2007 |
| WO | 2015/046216 A1 | 4/2015 |

OTHER PUBLICATIONS

Bhatia et al The FASEB Journal, vol. 13, Nov. 1999, pp. 1883-1900 (Year: 1999).*
Godbey et al., Biomaterials 25 (2004) 2799-2805 (Year: 2004).*
Griffith et al., Annals New York Academy of Sciences, Dec. 31, 1997; vol. 831: 382-397 (Year: 1997).*
Kim et al., Annals of Surgery, vol. 228, No. 1, pp. 8-13, Jul. 1998 (Year: 1998).*
Nishikawa et al., Journal of Biotechnology 133 (2008) 253-260 (Year: 2008).*
Kostadinova et al., Toxicology and Applied Pharmacology 268 (2013) 1-16 (Year: 2013).*
Knight et al., 3D Cell Culture: Methods and Protocols, Methods in Molecular Biology, vol. 695, Chapter20, pp. 323-340, John W. Haycock (ed.), 2011 (Year: 2011).*
Carnachan et al, Soft Mater. 2, 608-616 (2006) (Year: 2006).*
Qin et al., Physical Review B 90, 144424, pp. 1-21 (2014) (Year: 2014).*
Nichols et al., (Biomaterials 30 (2009) 1071-1079 (Year: 2009).*
Iwanaga et al., Fujifilm Research & Development (No. 54-2009), pp. 43-47 (Year: 2009).*

(Continued)

*Primary Examiner* — Evelyn Y Pyla
(74) *Attorney, Agent, or Firm* — Solaris Intellectual Property Group, PLLC

(57) ABSTRACT

Provided are a method for producing a cell tissue, including a culturing step of culturing cells capable of serving as a feeder inside opening pores and communicating pores of a porous film having a plurality of the opening pores provided on a surface thereof and the communicating pores communicating mutually adjacent opening pores with one another; and a porous film including a plurality of opening pores provided on a surface thereof and communicating pores communicating mutually adjacent opening pores with one another.

13 Claims, 19 Drawing Sheets

(56) References Cited

OTHER PUBLICATIONS

Nishikawa et al., International Journal of Nanoscience, vol. 1, Nos. 5 & 6 (2002) 415-418 (Year: 2002).*
WIPO English machine translation of priority document JP 2016-188627 (WO/2018/061846) (Year: 2022).*
Office Action dated Apr. 21, 2020, issued by the KIPO in corresponding Korean Patent Application No. 10-2019-7007676.
Morita, Yuka et al., "Response of Mesenchymal Stem Cells from Rat Adult Bone Marrow to Honeycomb-patternes Porous Polymer Films", Journal of the Surface Science Society of Japan, vol. 31, No. 8, 392-399, 2010 pp. 394-397.
Ishihata, H. et al., "Proliferation of Periodontal Ligament Cells on Biodegradable Honeycombs Film Scaffold with unified Micropore Organization", J. Biochem. Sci. Eng., 2010, 5(3): 252-261.
Tanaka, Masaru et al., "Honeycomb films for tissue engineering; design of tissue engineering scaffolds by self organization of polymers", Journal of Japanese Society for Biomaterials, vol. 24, No. 3: 152-161, May 2006 pp. 156, 157.
International Search Report issued in International Application No. PCT/JP2017/033605 dated Dec. 19, 2017.
Written Opinion of the ISA issued in International Application No. PCT/JP2017/033605 dated Dec. 19, 2017.
English language translation of the following: Office action dated Sep. 3, 2019 from the JPO in a Japanese patent application No. 2018-542409 corresponding to the instant patent application.
Extended European Search Report dated Sep. 17, 2019, issued in corresponding EP Patent Application No. 17855801.1.
English language translation of the following: Office action dated Oct. 30, 2020 from the KIPO in a Korean patent application No. 10-2019-7007676 corresponding to the instant patent application.
Freiman, A. et al., "Adipose-derived endothelial and mesenchymal stem cells enhance vascular network formation on three-dimensional constructs in vitro", Stem Cell Research & Therapy, (2016) 7:5.
Office Action dated Dec. 15, 2020, issued by the KIPO in corresponding Korean Patent Application No. 10-2019-7007676.
English language translation of the following: Office action dated Apr. 6, 2022 from the SIPO in a Chinese patent application No. 201780057813.6 corresponding to the instant patent application. This office action translation is submitted now in order to supplement the understanding of the cited references which are being disclosed in the instant Information Disclosure Statement.
Office Action dated Sep. 9, 2022, issued by the EPO in corresponding EP Patent Application No. 17855801.1.

\* cited by examiner

POROUS FILM     PMMA RING     CULTURE DEVICE

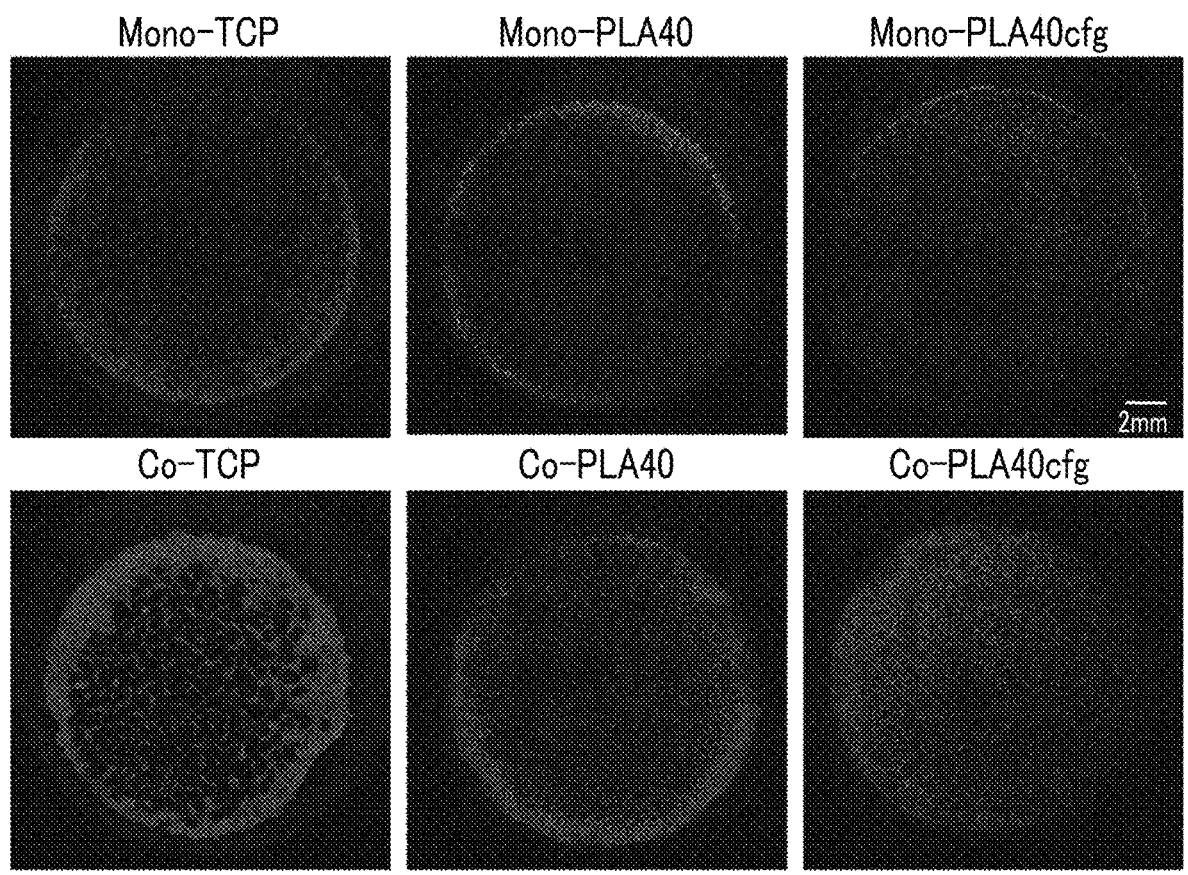

200 μm

200 μm

| | TCP | PLA40 |
|---|---|---|
| FULL IMAGE |  |  |
| ENLARGED IMAGE |  |  |

GREEN: HUVEC(CD31)

METHOD FOR PRODUCING CELL TISSUE, AND POROUS FILM

CROSS-REFERENCE TO RELATED APPLICATION

This application is a continuation application of International Application No. PCT/JP2017/033605, filed Sep. 15, 2017, the disclosure of which is incorporated herein by reference in its entirety. Further, this application claims priority from Japanese Patent Application No. 2016-188627, filed Sep. 27, 2016, the disclosure of which is incorporated herein by reference in its entirety.

BACKGROUND OF THE INVENTION

1. Field of the Invention

The present disclosure relates to a method for producing a cell tissue and a porous film to be used for the production of a cell tissue.

2. Description of the Related Art

A filter for enriching cells, a scaffold for growing cells, and a graft material for engraftment of cells and transplantation thereof into a living body, which are used for the purpose of transplanting cells or cell tissues into a living body, are known.

For example, JP2012-006010A discloses a composite porous membrane that separates a target cell by size. For example, WO2006/093207A discloses a culture substrate in which pores are arranged in a honeycomb shape on the cell culture surface. For example, JP2005-110709A discloses a bone prosthetic material in which through-pores and communicating pores are combined, as a bone prosthetic material that engrafts bone marrow mesenchymal stem cells and induces differentiation thereof into osteoblasts and then transplants the osteoblasts into a bone defect portion. For example, JP2004-216119A discloses a porous support having a structure in which pores having long shapes in the thickness direction are arranged in parallel in the plane direction and the pores are communicated through small pores, as a scaffold for engraftment and proliferation of cells. For example, JP2008-199962A discloses a spheroid forming substrate in which a plurality of cell adhesive regions and cell non-adhesive regions surrounding the cell adhesive regions are arranged on the surface of a porous film having a three dimensional network structure. For example, JP2001-523483A discloses a porous polymer scaffold including interconnected pores, as a scaffold for engraftment and proliferation of osteogenic cells. For example, JP2008-307180A discloses a scaffold including a lamination of struts arranged in a longitudinal and lateral lattice shape, as a graft material for injecting stem cells into the inside of a structure and transplanting the same into a living body. For example, JP4437227B discloses an artificial blood vessel including a tubular porous body made of a water-insoluble polymer, vascular endothelial cells covering the inner surface of the tubular porous body, and vascular smooth muscle cells covering the outer surface of the tubular porous body.

SUMMARY OF THE INVENTION

Currently, a cell tissue with a relatively simple structure such as skin or cartilage is artificially created and is used in the field of medical transplantation. On the other hand, practical application of an artificial cell tissue substituting an organ in which various cells form a complicated structure, such as liver or pancreas, is expected, but for this purpose, it is necessary to prepare a cell tissue having organ-specific cells functionally arranged and comprising a vascular network and a lymphatic network. In addition, as a test cell tissue replacing an animal experiment or a clinical test, a cell tissue having a structure resembling an organ in a living body is awaited.

The present disclosure was made under the foregoing circumstances.

An object of the present disclosure is to provide a production method for producing a cell tissue comprising a micro-order network structure, and a porous film to be used for the production of a cell tissue comprising a micro-order network structure.

Specific means for achieving the foregoing object includes the following aspects.

[1] A method for producing a cell tissue, comprising a culturing step of culturing cells capable of serving as a feeder inside opening pores and communicating pores of a porous film having a plurality of the opening pores provided on a surface thereof and the communicating pores communicating mutually adjacent opening pores with one another.

[2] The method for producing a cell tissue according to [1], in which the culturing step is a culturing step of co-culturing the cells capable of serving as a feeder and at least one of vascular endothelial cells or lymphatic endothelial cells inside the opening pores and the communicating pores.

[3] The method for producing a cell tissue according to [1], in which the culturing step is a culturing step of co-culturing the cells capable of serving as a feeder and cells forming a parenchymal organ inside the opening pores and the communicating pores.

[4] The method for producing a cell tissue according to [1], in which the culturing step is a culturing step of co-culturing the cells capable of serving as a feeder, cells forming a parenchymal organ, and at least one of vascular endothelial cells or lymphatic endothelial cells inside the opening pores and the communicating pores.

[5] The method for producing a cell tissue according to any one of [1] to [4], in which the cells capable of serving as a feeder are at least one of mesenchymal stem cells or fibroblasts.

[6] The method for producing a cell tissue according to any one of [1] to [5], in which the plurality of opening pores are arranged in a honeycomb shape on the surface of the porous film.

[7] The method for producing a cell tissue according to any one of [1] to [6], in which the communicating pores are provided at substantially the same depth over an entire area of the porous film in a plane direction.

[8] The method for producing a cell tissue according to any one of [1] to [7], in which a pore diameter of the communicating pore is in a range of 50% to 500% of a major axis of the cell seeded on the porous film.

[9] The method for producing a cell tissue according to any one of [1] to [8], in which a pore diameter of the communicating pore is in a range of 5 μm to 50 μm.

[10] The method for producing a cell tissue according to any one of [1] to [9], in which a variation coefficient of a pore diameter of the communicating pore is 30% or less.

[11] The method for producing a cell tissue according to any one of [1] to [10], in which a major axis of the opening pore in a plane direction of the porous film is in a range of 10 μm to 100 μm.

[12] The method for producing a cell tissue according to any one of [1] to [11], in which a depth of the opening pore is in a range of 10 μm to 100 μm.

[13] The method for producing a cell tissue according to any one of [1] to [12], in which an opening diameter of the opening pore is in a range of 5 μm to 90 μm.

[14] The method for producing a cell tissue according to any one of [1] to [13], in which a variation coefficient of an opening diameter of the opening pore is 20% or less.

[15] The method for producing a cell tissue according to any one of [1] to [14], further comprising, prior to the culturing step, a centrifugation step of seeding the cells on a surface of the porous film on a side where the plurality of opening pores are opened, and then applying a centrifugal force in a direction from a surface seeded with the cells to an opposite surface to move the cells to the inside of the plurality of opening pores.

[16] A porous film comprising a plurality of opening pores provided on a surface thereof and communicating pores communicating mutually adjacent opening pores with one another, in which a major axis of the opening pore in a plane direction of the porous film is in a range of 20 μm to 100 μm.

[17] A porous film comprising a plurality of opening pores provided on a surface thereof and communicating pores communicating mutually adjacent opening pores with one another, in which a depth of the opening pore is in a range of 20 μm to 100 μm.

[18] The porous film according to [16] or [17], in which an opening diameter of the opening pore is in a range of 5 μm to 90 μm.

[19] The porous film according to any one of [16] to [18], in which a pore diameter of the communicating pore is in a range of 5 μm to 50 μm.

[20] The porous film according to any one of [16] to [19], in which the plurality of opening pores are arranged in a honeycomb shape on the surface of the porous film.

According to the present disclosure, there are provided a production method for producing a cell tissue comprising a micro-order network structure, and a porous film to be used for the production of a cell tissue comprising a micro-order network structure.

BRIEF DESCRIPTION OF THE DRAWINGS

FIG. 7A is a fluorescent immunostaining image (low magnification) of CD31 in cells on Day 3 of culture in which vascular endothelial cells are cultured alone or mesenchymal stem cells and vascular endothelial cells are co-cultured.

DESCRIPTION OF THE PREFERRED EMBODIMENTS

Figure 1A:
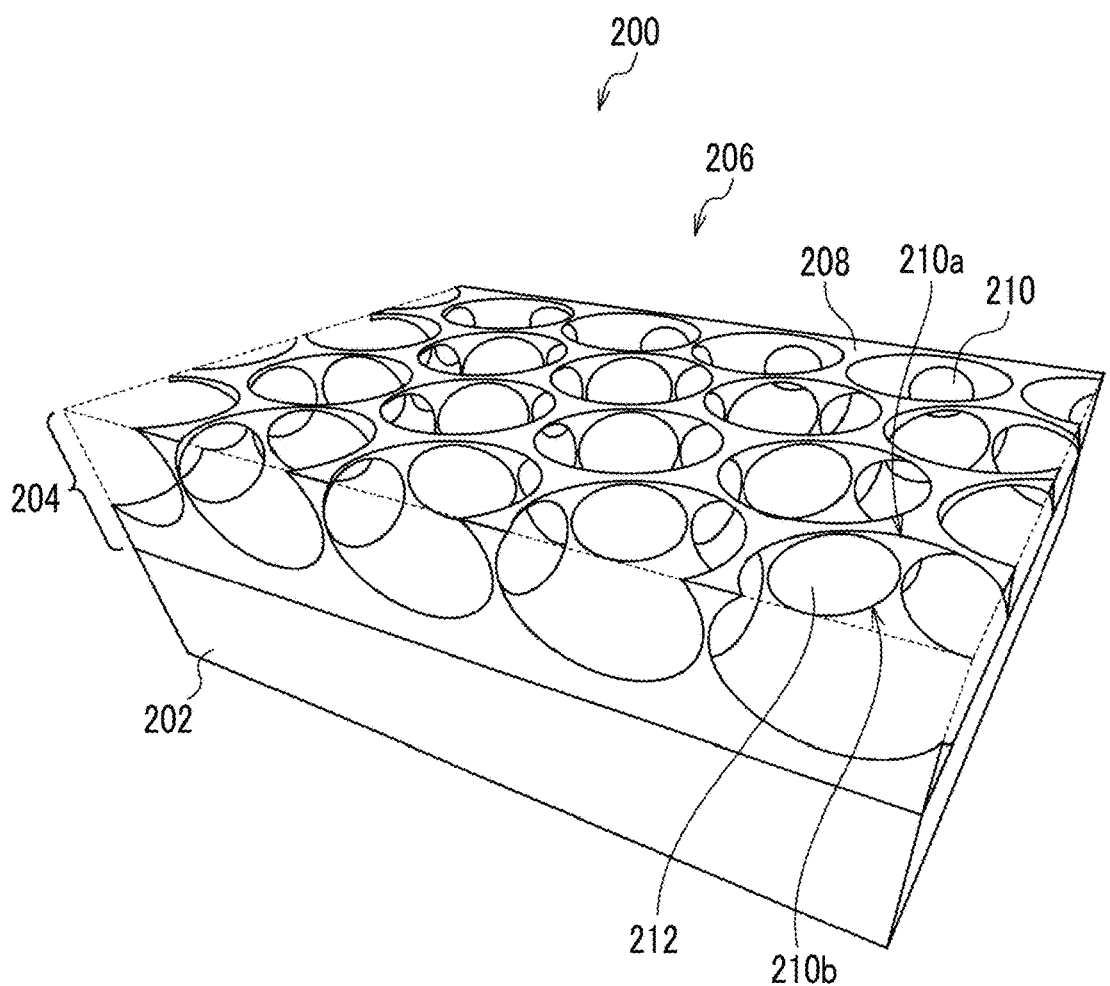
FIG. 1A is a perspective view showing a structure of a porous film.

Hereinafter, embodiments of the present disclosure will be described. These descriptions and examples are illustrative of embodiments and do not limit the scope of the invention.

The numerical range indicated by using "to" in the present disclosure indicates a range including numerical values described before and after "to" as a lower limit value and an upper limit value, respectively.

The term "step" in the present disclosure includes not only an independent step but also a step in which the intended purpose of this step can be achieved even in the case where the step cannot be clearly distinguished from other steps.

In the present disclosure, upon referring to an amount of each component in a composition, in the case where there are a plurality of substances corresponding to each component in the composition, the amount means a total amount of the plurality of substances present in the composition unless otherwise specified.

In the present disclosure, the variation coefficient is expressed in terms of percentage. The variation coefficient is a value obtained by dividing the standard deviation by a mean value for a certain population and is an index showing the degree of variation of the population.

<Porous Film>

The method for producing a cell tissue of the present embodiment is a method for producing a cell tissue ex vivo and includes a culturing step of culturing cells inside opening pores and communicating pores of a porous film having a plurality of the opening pores provided on a surface thereof and the communicating pores communicating mutually adjacent opening pores with one another. First, a porous film to be used for the production of a cell tissue will be described. The porous film of the present embodiment functions as a scaffold for cells to engraft and form tissues.

The porous film of the present embodiment has a plurality of opening pores provided on the surface thereof and communicating pores communicating the adjacent opening pores with one another. The wall surfaces of the opening pores and the communicating pores provided in the porous film serve as scaffolds for cells to engraft. Cells seeded on the porous film of the present embodiment engraft within the opening pores and the communicating pores to form a cell tissue comprising a micro-order network structure.

Hereinafter, an example of the porous film will be described with reference to the drawings. In the drawings, the same or equivalent constituent elements and parts are given the same reference numerals. In the following description, the term "plane direction" means a main plane direction of the porous film, and the term "thickness direction" means a thickness direction of the porous film. In the following description, "major axis" means a maximum length among any two-point distances on the contour, but in the case where the direction is specified, it means a maximum length among any two-point distances in that direction. In the following description, the term "center of the opening" means the center of gravity in the case where the opening is taken as a two-dimensional figure in the plane direction.

Figure 1B:
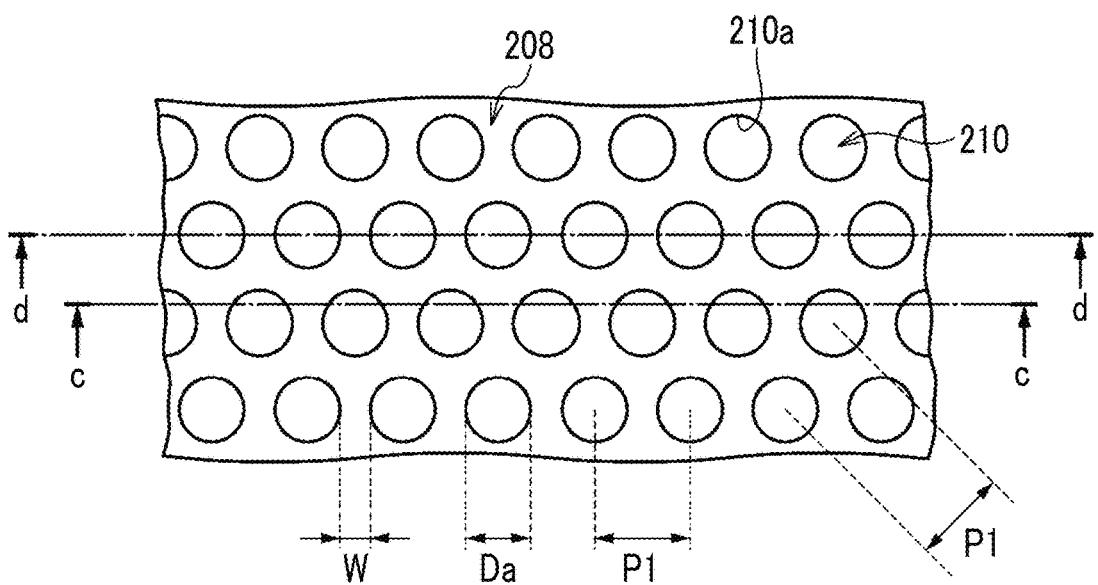
FIG. 1B is a plan view seen from the opening surface side in FIG. 1A.
Figure 1C:
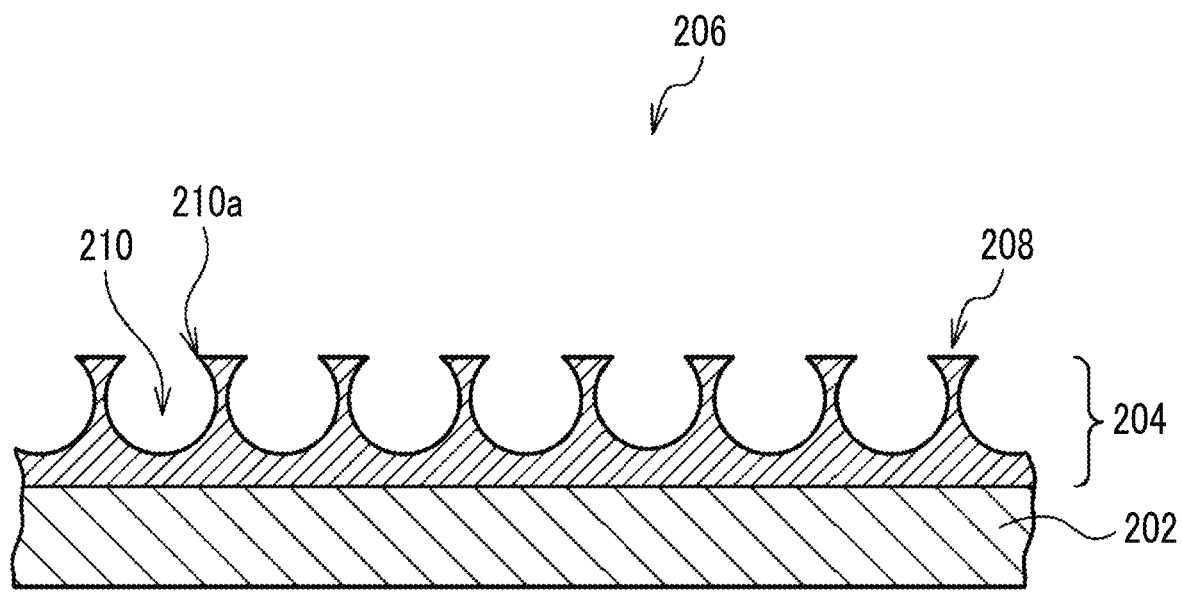
FIG. 1C is a cross-sectional view taken along a line c-c in FIG. 1B.
Figure 1D:
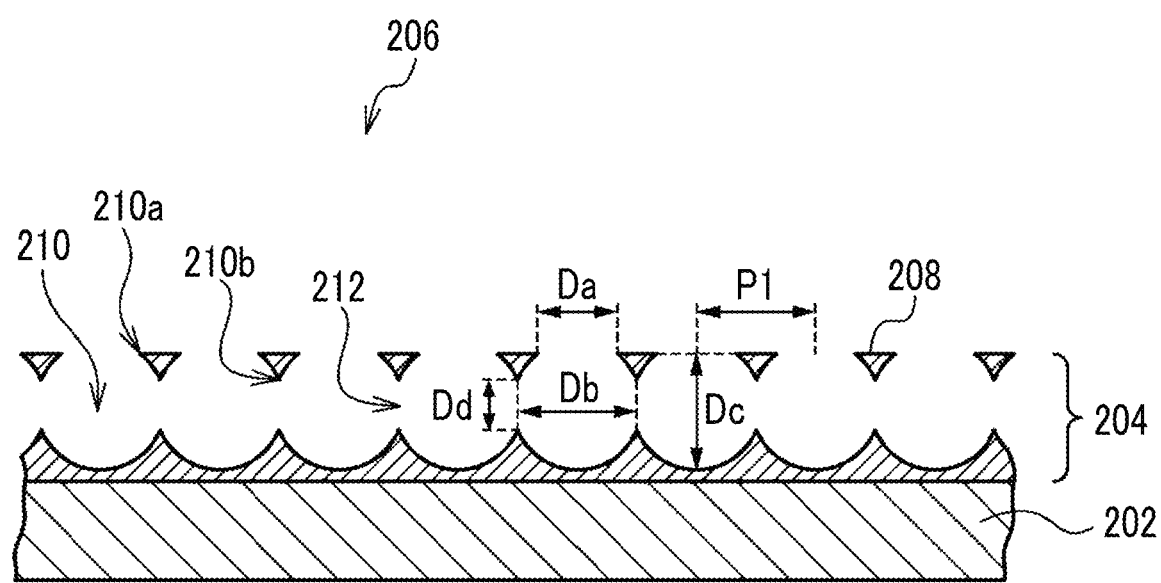
FIG. 1D is a cross-sectional view taken along a line d-d in FIG. 1B.

FIG. 1A is a perspective view showing the structure of the porous film, FIG. 1B is a plan view seen from the opening surface side in FIG. 1A, FIG. 1C is a cross-sectional view taken along a line c-c in FIG. 1B, and FIG. 1D is a cross-sectional view taken along a line d-d in FIG. 1B. FIGS. 1A to 1D show a porous film 200 which is an example of the present embodiment.

The porous film 200 is a laminate comprising a porous layer 204 in which a plurality of opening pores 210 are arranged in the plane direction and a support 202 for supporting the porous layer 204. As another example, the porous film 200 may not be provided with the support 202 and may be a monolayer structure of only the porous layer 204.

In the porous layer 204 of the porous film 200, the opening pores 210 are arranged over an entire area in a plane direction. However, in the case where there is a region where the cells cannot come into contact with the porous layer 204, the opening pores 210 may not be arranged in the region.

An opening surface 206 of the porous film 200 is the surface on the side where the plurality of opening pores 210 are opened and is the surface on the side where the cells are seeded. In the opening surface 206, the openings of opening pores 210 adjacent to one another are spaced apart by flat portions 208 extending among opening portions 210a. A liquid medium is supplied to the inside of the opening pores 210 and the communicating pores 212 through the openings of the opening pores 210 in the opening surface 206.

Each of the opening pores 210 is a bottomed pore not penetrating the porous layer 204. As another example, each of the opening pores 210 may be a bottomed pore penetrating the porous layer 204 and having the surface of the support 202 as a bottom surface. In the example where the porous film 200 is a monolayer structure of the porous layer 204, each of the opening pores 210 may be a bottomed pore that does not penetrate the porous layer 204 or may be a through-pore penetrating the porous layer 204.

As the shape of each of the opening pores 210, for example, a spherical shape obtained by cutting a part of a sphere, a barrel shape, a cylindrical shape, or a prismatic shape can be mentioned. As the shape of the opening of each opening pore 210, for example, a circle, an ellipse, or a polygon can be mentioned.

The plurality of opening pores 210 are regularly arranged, specifically, they are arranged in a honeycomb shape. As another example, the plurality of opening pores 210 may be arranged in a lattice shape or a face-centered lattice shape. The arrangement of the plurality of opening pores 210 may be random, but the plurality of opening pores 210 are preferably regularly arranged from the viewpoint of making the density of the opening pores 210 uniform in the plane direction and therefore enhancing the homogeneity of the tissue formed by the cells in the porous film 200. Regular arrangement may be discontinuous or misaligned, but it is preferred that the arrangement is repeated continuously without gaps in all directions. The honeycomb-like arrangement refers to an arrangement in which a parallelepiped shape (preferably a regular hexagon) or a shape close thereto is used as a unit and the center of gravity of the opening is located at the apexes and the intersection of diagonal lines of these figures. The lattice-like arrangement refers to an arrangement in which a parallelogram shape (needless to say, including square, rectangle, and rhomboid, preferably square) or a shape close thereto is used as a unit and the center of gravity of the opening is located at the apexes of these figures. The face-centered lattice-like arrangement refers to an arrangement in which a parallelogram shape (needless to say, including square, rectangle, and rhomboid, preferably square) or a shape close thereto is used as a unit and the center of gravity of the opening is located at the apexes and the intersection of diagonal lines of these figures. As a measure of being arranged regularly, regarding the area of the parallelepiped shape or the parallelogram shape which is the unit of arrangement, its variation coefficient is 10% or less.

In the porous film 200, the mutually adjacent opening pores 210 communicate with one another through the communicating pores 212 inside the porous layer 204. It is preferred that one opening pore 210 communicates with all adjacent opening pores 210. In the porous film 200 in which the plurality of opening pores 210 are arranged in a honeycomb shape, it is preferred that one opening pore 210 communicates with six adjacent opening pores 210, that is, it is preferred that one opening pore 210 preferably has six communicating pores 212.

In the porous film 200, the mutually adjacent opening pores 210 are arranged such that a part of each wall surface is continuous, and the communicating pore 212 is a pore surrounded by a connecting portion 210b between the opening pores 210. As another example, the adjacent opening pores 210 are independent from one another, and the communicating pore 212 which is a cylindrical gap may connect the adjacent opening pores 210 to one another.

Hereinafter, the dimensions of the structure of the porous film 200 will be described.

The plurality of opening pores 210 have such a size that the cells seeded on the porous film 200 can enter and engraft. The major axis of the cells seeded on the porous film 200 is, for example, 10 μm to 50 μm.

The opening diameter Da of the opening pore 210 is preferably 50% or more, more preferably 80% or more, and still more preferably 120% or more, with respect to the major axis of the cell seeded on the porous film 200. In the case where the opening diameter Da is 50% or more (more preferably 80% or more, and still more preferably 120% or more), the cells seeded on the porous film 200 can enter the inside of the opening pore 210. Specifically, the opening diameter Da of the opening pore 210 is preferably 5 μm or more, more preferably 8 μm or more, and still more preferably 12 μm or more. The opening diameter Da of the opening pore 210 is preferably 90 μm or less, more preferably 70 μm or less, and still more preferably 50 μm or less, depending on the relationship with the preferable arrangement and size of the opening pore 210. The opening diameter Da is the major axis of the opening of the opening pore 210, and the range of the opening diameter Da is confirmed by measuring the opening diameters of 10 or more selected openings.

The variation coefficient of the opening diameter Da of the opening pore 210 is preferably 20% or less, and is preferably as small as possible. The smaller the variation coefficient of the opening diameter Da, the higher the homogeneity of the tissue formed by the cells in the porous film 200.

In the cell culture region of the porous film 200, the ratio of the total area of the openings of the opening pores 210 to the total area of the opening surface 206 is preferably 20% to 90%, more preferably 30% to 80%, and still more preferably 40% to 70%.

The major axis Db in the plane direction of the opening pore 210 is preferably in the range of 10 μm to 100 μm, more preferably in the range of 20 μm to 80 μm, and still more preferably in the range of 30 μm to 60 μm. In the case where the major axis Db is 10 μm or more (more preferably 20 μm or more, and still more preferably 30 μm or more), a space for the proliferation of proliferating cells is secured and a space in which a plurality of types of co-cultured cells coexist is secured. In the case where the major axis Db is 100 μm or less (more preferably 80 μm or less, and still more preferably 60 μm or less), it is possible to form a micro-order network structure. The major axis Db is a major axis in the plane direction of the contour of the opening pore 210 appearing on the cut surface obtained by cutting the opening pore 210 on the major axis of the opening (that is, on the opening diameter Da) and in the thickness direction. In the porous film 200 in which a plurality of opening pores 210 having an isotropic shape and substantially the same size (including the same size) in the plane direction are arranged in a honeycomb shape having a regular hexagonal shape or a shape close thereto as a unit, and the mutually adjacent opening pores 210 are arranged such that part of each wall surface is continuous, a center-to-center distance P1 between the mutually adjacent openings is regarded as the major axis Db. In this case, the range of the major axis Db is confirmed by measuring the center-to-center distance P1 in total of 10 or more in three directions whose angles are shifted by approximately 60 degrees (including 60 degrees). Regarding porous films having an arrangement other than the above-mentioned arrangement, the range of the major axis Db is confirmed according to the regularity of the arrangement of the opening pores 210 in accordance with the above.

A depth Dc of the opening pore 210 is preferably in the range of 10 μm to 100 μm, more preferably in the range of 20 μm to 80 μm, and still more preferably in the range of 30 μm to 60 μm. In the case where the depth Dc of the opening pore 210 is 10 μm or more (more preferably 20 μm or more, and still more preferably 30 μm or more), a space for the proliferation of proliferating cells is secured and a space in which a plurality of types of co-cultured cells coexist is secured. In the case where the depth Dc of the opening pore 210 is 100 μm or less (more preferably 80 μm or less, and still more preferably 60 μm or less), it is possible to form a micro-order network structure. The depth Dc is a distance from the opening surface 206 to the deepest portion of the opening pore 210 in each of the opening pores 210. In the porous film 200 in which the plurality of opening pores 210 are arranged in a honeycomb shape having a regular hexagonal shape or a shape close thereto as a unit, the distance from the opening surface 206 to the deepest portion of the opening pore 210 in the contour of the opening pore 210 appearing on the cut surface in the thickness direction on the line connecting the centers of the openings is defined as the depth Dc. In this case, the range of the depth Dc is confirmed by forming three cut surfaces in which the angle of the cutting line is shifted by approximately 60 degrees (including 60 degrees), and measuring the distance from the opening surface 206 to the deepest portion of the opening pore 210 in total of 10 or more.

A pore diameter Dd of the communicating pore 212 is preferably in the range of 50% to 500% of the major axis of the cell seeded on the porous film 200. In the case where the pore diameter Dd of the communicating pore 212 is 50% or more of the major axis of the seeded cell, the cells can move among the mutually adjacent opening pores 210. From this point of view, the pore diameter Dd of the communicating pore 212 is more preferably 80% or more and still more preferably 120% or more of the major axis of the seeded cell. On the other hand, in the case where the pore diameter Dd of the communicating pore 212 is 500% or less of the major axis of the seeded cell, the number of cells engrafting into the communicating pore 212 becomes appropriate. From this point of view, the pore diameter Dd of the communicating pore 212 is more preferably 400% or less and more preferably 300% or less of the major axis of the seeded cell.

In view of the above, the pore diameter Dd of the communicating pore 212 is preferably in the range of 5 μm to 50 μm, more preferably in the range of 8 μm to 45 μm, and still more preferably in the range of 12 μm to 40 μm. The pore diameter Dd is a major axis in the thickness direction in the contour of the communicating pore 212 appearing on the cut surface in the thickness direction on the line connecting the centers of the openings. In the porous film 200 in which the plurality of opening pores 210 are arranged in a honeycomb shape having a regular hexagonal shape or a shape close thereto as a unit, the range of the pore diameter Dd is confirmed by forming three cut surfaces in which the angle of the cutting line is shifted by approximately 60 degrees (including 60 degrees), and measuring the pore diameter Dd in total of 10 or more. Regarding porous films having an arrangement other than the above-mentioned arrangement, the range of the pore diameter Dd is confirmed by forming cut surfaces according to the regularity of the arrangement of the opening pores 210 in accordance with the above.

The variation coefficient of the pore diameter Dd of the communicating pore 212 is preferably 30% or less and more preferably 20% or less, and is preferably as small as possible. The smaller the variation coefficient of the pore diameter Dd, the higher the homogeneity of the tissue formed by the cells in the porous film 200.

It is preferred that the communicating pores 212 are provided at substantially the same depth (including the same depth) over an entire area in a plane direction. Thereby, the homogeneity of the tissue formed by the cells in the porous film 200 is secured. The indication of "substantially the same" is that the variation coefficient of the distance from the opening surface 206 to the deepest portion of the communicating pore 212 on the cut surface for measuring the pore diameter Dd is 10% or less.

A width W of the flat portion 208 is preferably narrower than the major axis of the cell. This reduces the proportion of cells cultured on the flat portion 208 and increases the proportion of cells cultured inside the opening pores 210 and the communicating pores 212. The width W is a length of the flat portion 208 which is measured between the centers of the openings.

Hereinafter, the material of the porous film 200 will be described. The material of the porous film 200 is selected from the viewpoint of cell adhesiveness, affinity with a transplant site in a living body, difficulty in decomposition or absorption in a living body, and the like.

As the material of the porous layer 204, a hydrophobic polymer soluble in a hydrophobic organic solvent is preferable from the viewpoint of producing the porous film 200 by a production method which will be described later. The hydrophobic organic solvent is a liquid having a solubility in water at 25° C. of 10 (g/100 g water) or less.

Examples of the hydrophobic polymer include polymers such as polystyrene, polyacrylate, polymethacrylate, polyacrylamide, polymethacrylamide, polyvinyl chloride, polyvinylidene chloride, polyvinylidene fluoride, polyhexafluoropropane, polyvinyl ether, polyvinyl carbazole, polyvinyl acetate, polytetrafluoroethylene, polyester (for example, polyethylene terephthalate, polyethylene naphthalate, polyethylene succinate, polybutylene succinate, polylactic acid, or poly-3-hydroxybutyrate), polylactone (for example, polycaprolactone), polyamide or polyimide (for example, nylon or polyamide acid), polyurethane, polyurea, polybutadiene, polycarbonate, polyaromatics, polysulfone, polyethersulfone, polysiloxane derivatives, and cellulose acrylate (for example, triacetyl cellulose, cellulose acetate propionate, or cellulose acetate butyrate). These polymers may be homopolymers, copolymers, polymer blends, or polymer alloys, if necessary, from the viewpoints of solubility in solvents, optical properties, electrical properties, film hardness, elasticity, and the like. These polymers may be used alone or in admixture of two or more thereof. From the viewpoint of bioabsorbability, polylactic acid, polycaprolactone, poly-3-hydroxybutyrate, and the like are preferable.

The material of the support 202 may be the same as or different from that of the porous layer 204. Examples of the material of the support 202 include synthetic resin, glass, and metal. In the case of being used for the production of a cell tissue or in the case of peeling the porous layer 204 from the support 202 after the production of the cell tissue, the material of the support 202 is preferably a material different from that of the porous layer 204.

Figure 2:
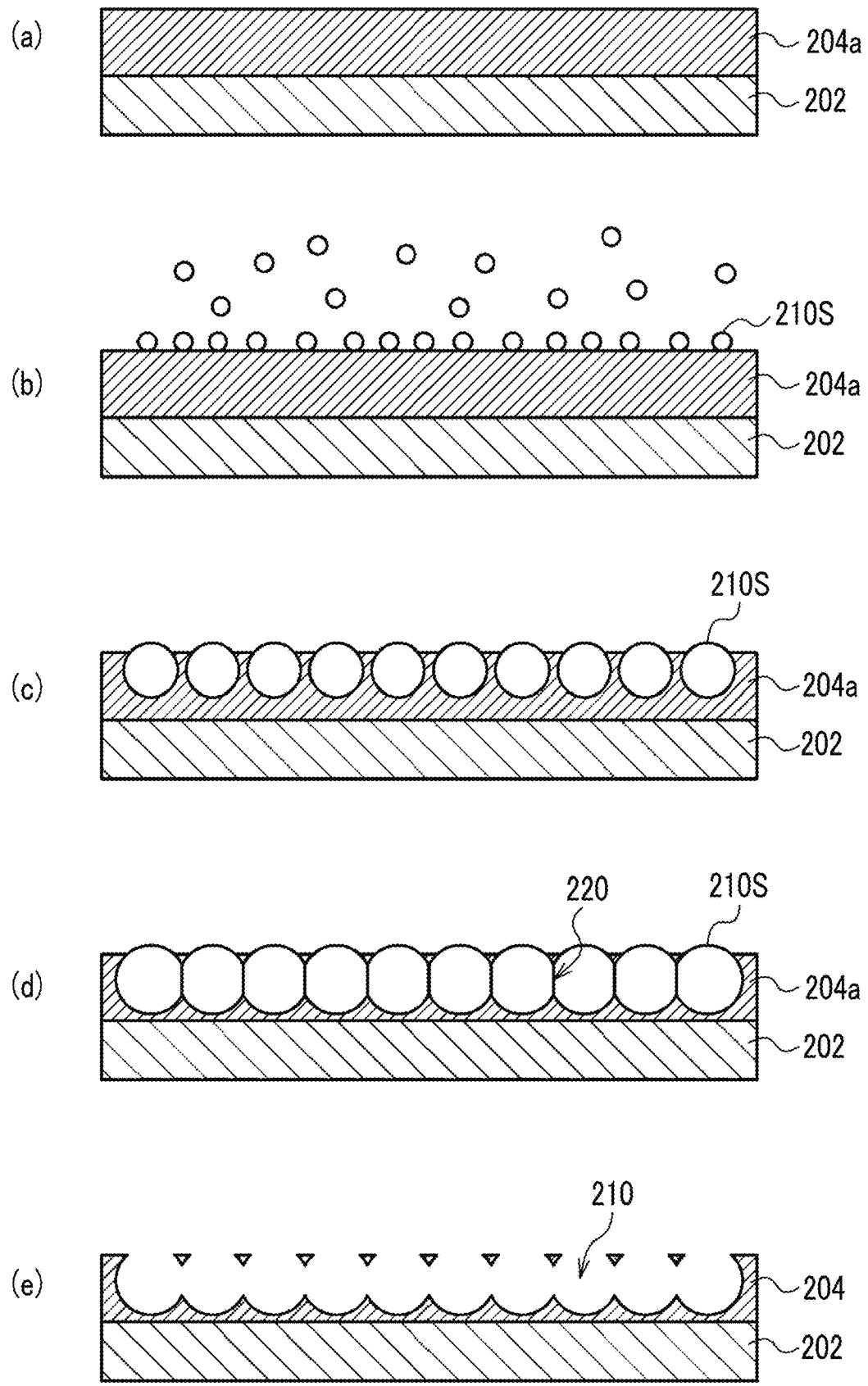
FIG. 2 is a schematic view showing an example of a method for producing a porous film.

The porous film 200 is produced by, for example, a production method in which the following steps (a) to (e) are carried out in order. FIG. 2 is a schematic view showing a cross section of the porous film 200 in steps (a) to (e).

[Step (a)]

A coating liquid prepared by dissolving a hydrophobic polymer constituting the porous layer 204 in a solvent is prepared and the coating liquid is applied onto the support 202 to form a coating film 204a on the support 202.

The coating liquid is prepared by mixing a hydrophobic polymer, a solvent, and an amphiphilic compound. The solvent is preferably a mixed solvent of a good solvent for a hydrophobic polymer and a hydrophobic liquid, or a hydrophobic organic solvent which is a good solvent for a hydrophobic polymer. Examples of the latter include halogen-based solvents such as trichloromethane, dichloromethane, and chloroform, in which these solvents may be used in admixture with hydrocarbon compounds such as n-hexane, cyclohexane, n-pentane, n-octane, and n-heptane which are hydrophobic liquids.

The amphiphilic compound is a compound having both a hydrophilic group and a hydrophobic group. In the case where the amphiphilic compound is blended in a coating liquid, it is easy to form water droplets on the surface of the coating film. Further, by controlling the dispersion state of the hydrophobic polymer with respect to the solvent with the amphiphilic compound, it is possible to more easily control the growth of water droplets. Examples of the amphiphilic compound include many sorts of commercially available surfactants, oligomers such as dimers and trimers, and high molecular weight compounds such as polymers. Specific examples of the amphiphilic compound include compounds having a polyacrylate skeleton as a main chain and having a long chain aliphatic group (for example, a dodecyl group) as a lipophilic side chain and a carboxyl group as a hydrophilic side chain; polyethylene glycol/polypropylene glycol block copolymers; and phospholipids.

In the coating liquid, the concentration of the hydrophobic polymer is preferably 0.1% by mass to 10% by mass, and the concentration of the amphiphilic compound is preferably 0.01% by mass to 1% by mass.

[Step (b)]

Humidified air is allowed to flow over the entire surface of the coating film 204a to form water droplets 210S on the coating film 204a due to dew condensation. At this time, at least one of dew point Td of the humidified air or surface temperature Ts of the coating film 204a is controlled so that the difference $\Delta T$ (=Td−Ts) between the dew point Td of the humidified air flowing in the vicinity of the coating film 204a and the surface temperature Ts of the coating film 204a satisfies Expression (1).

$$3° C. \leq \Delta T \leq 30° C. \qquad \text{Expression (1)}$$

[Step (c)]

Water droplets 210S are grown by continuing the supply of humidified air. Each of the water droplets 210S grows to substantially the same size (including the same size). With the evaporation of the solvent contained in the coating film 204a, the water droplets 210S are arranged in a honeycomb shape by the transverse capillary force and enter the coating film 204a. In parallel with this, as the solvent contained in the coating film 204a evaporates, the hydrophobic polymer precipitates around the water droplets 210S.

[Step (d)]

The supply of the humidified air is continued to grow the water droplets 210S until the water droplets 210S are brought into close contact with one another with amphiphilic compound films 220 interposed therebetween in the coating film 204a.

[Step (e)]

Simultaneously with or after evaporation of the solvent, the water droplets 210S are evaporated so that the portion where the water droplets 210S enter the coating film 204a is left as the opening pore 210, and in parallel, the amphiphilic compound films 220 that separate the closely adjacent water droplets 210S are destroyed. This results in the formation of the porous layer 204 in which a plurality of opening pores 210 are arranged in a honeycomb shape and connected inside.

Figure 3:
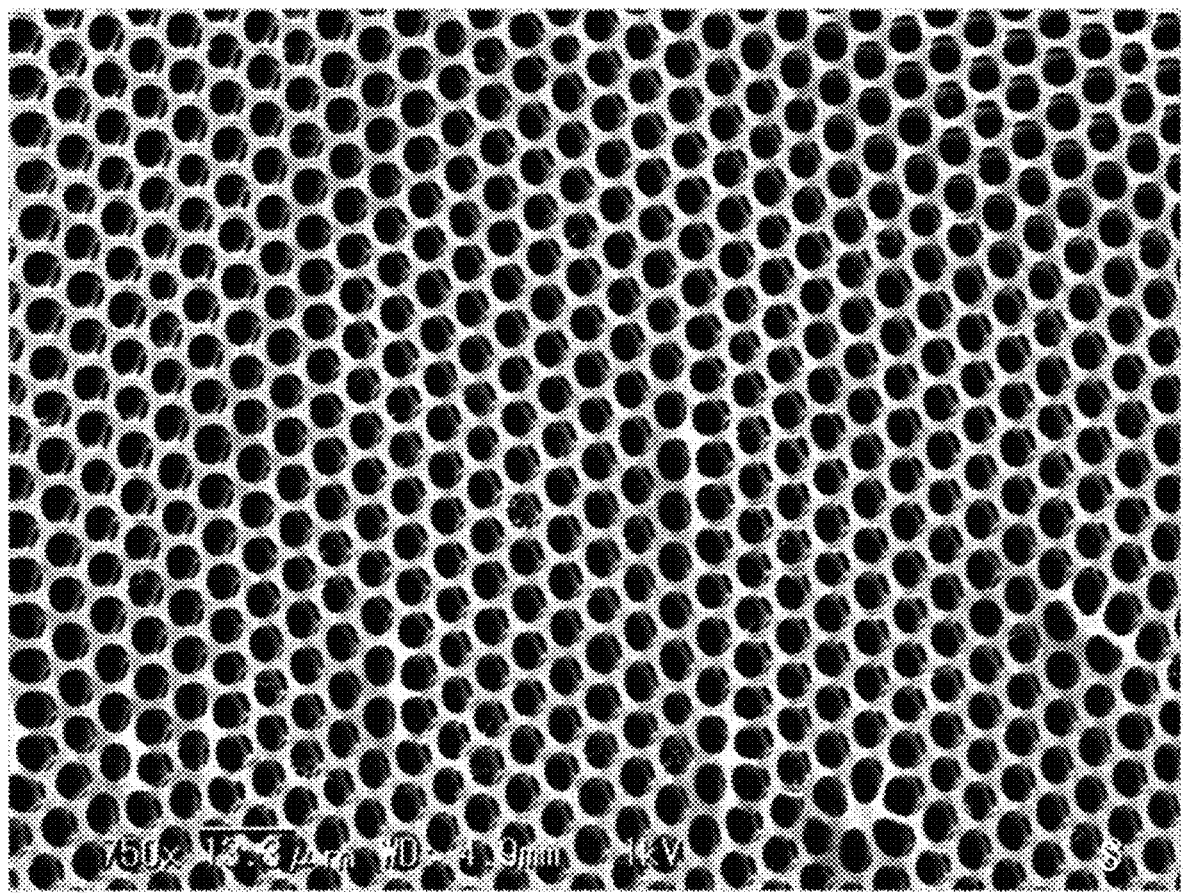
FIG. 3 is a scanning electron microscope image of the porous film.

Through the above steps (a) to (e), a laminate of the porous layer 204 and the support 202 is obtained. The laminate of the porous layer 204 and the support 202 may be used as the porous film 200; the porous layer 204 may be peeled from the support 202, and then the monolayer structure of the porous layer 204 may be used as the porous film 200; or the porous layer 204 may be peeled from the support 202 and attached to another support to form the porous film 200. A charge treatment by plasma discharge or the like may be carried out on the surface of the porous film 200 on which the cells are seeded. FIG. 3 is a micrograph of an example of a porous film produced through the steps (a) to (e) taken from the side of an opening surface using a scanning electron microscope.

The opening diameter Da, the major axis Db, and the depth Dc of the opening pore 210 and the pore diameter Dd of the communicating pore 212 can be controlled by adjusting the size of the water droplets 210S. The size of the water droplets 210S can be adjusted by the film thickness of the coating film 204a, the amount of water vapor contained in the humidified air, and the timing at which the water droplets 210S are evaporated.

According to the above-mentioned production method, it is possible to produce a porous film in which a plurality of opening pores are arranged with high uniformity in a honeycomb shape without using a mold or a mask. The details of the above-mentioned production method are described in, for example, JP2007-291367A, JP2009-256624A, JP2011-074140A, and JP2011-202100A. The porous film 200 can also be produced by etching, sandblasting, press molding, or the like.

<Method for Producing Cell Tissue>

The method for producing a cell tissue of the present embodiment is a production method for producing a cell tissue ex vivo and includes a culturing step of culturing the cells inside the opening pores and the communicating pores of the porous film of the present disclosure. Hereinafter, the opening pores and the communicating pores of the porous film are collectively referred to as "pores".

According to the present embodiment, a cell tissue comprising a micro-order network structure is formed since the pores of the porous film of the present disclosure act as a trajectory in which cells are arranged in a micro-order network shape. The cell tissue comprising a micro-order network structure is useful as a graft material in vivo and as a test cell tissue replacing an animal experiment or a clinical test. The cell tissue may be used per porous film or may be used by removing the flat portion around the opening of the porous film and taking it out of the pore of the porous film. The cell tissue may also be used in the form of a laminate of a plurality of cell tissues.

The culturing step of the present embodiment includes the following embodiments (1) to (4).

Embodiment (1)

A Culturing Step of Culturing Cells Capable of Serving as a Feeder Alone

However, cells capable of serving as a feeder may be of one type or two or more types.

According to the embodiment (1), a cell tissue comprising a network structure of feeder cells is provided. The cell tissue produced according to the embodiment (1) is used, for example, as a scaffold in the case where cell culture is carried out ex vivo, or as a scaffold which is transplanted into a living body to regenerate tissues at a transplant site.

Examples of cells capable of serving as a feeder include mesenchymal stem cells and fibroblasts. The mesenchymal stem cells (MSCs) are somatic stem cells that can differentiate into myocytes, adipocytes, chondrocytes, or the like, and are also known to serve as a feeder. It is also possible to differentiate mesenchymal stem cells into somatic cells (for example, myocytes, adipocytes, or chondrocytes) by adding a differentiation-inducing factor for mesenchymal stem cells to a medium in the culturing step. In this case, for example, a muscle tissue, adipose tissue, or cartilage tissue comprising a micro-order network structure is provided.

Embodiment (2)

A Culturing Step of Co-Culturing Cells Capable of Serving as a Feeder and at Least One of Vascular Endothelial Cells or Lymphatic Endothelial Cells According to the embodiment (2), a cell tissue comprising a network structure of vascular endothelial cells or lymphatic endothelial cells is provided. The cell tissue produced according to the embodiment (2) is used, for example, as a scaffold in the case where culture of somatic cells is carried out ex vivo, or as a scaffold which is transplanted into a living body to regenerate tissues at a transplant site.

Examples of vascular endothelial cells include vascular endothelial cells derived from umbilical cord vein, umbilical cord artery, aorta, coronary artery, pulmonary artery, pulmonary microvessel, dermal microvessel, and the like, and vascular endothelial cells differentiated from pluripotent stem cells. Examples of lymphatic endothelial cells include lymphatic endothelial cells derived from dermal micro-lymphatic vessels, pulmonary micro-lymphatic vessels, and the like, and lymphatic endothelial cells differentiated from pluripotent stem cells. It is possible to control proliferation, migration, and tube formation of vascular endothelial cells or lymphatic endothelial cells by changing the composition of the medium in the culturing step.

Embodiment (3)

A Culturing Step of Co-Culturing Cells Capable of Serving as a Feeder and Cells Forming A Parenchymal Organ According to the embodiment (3), a cell tissue comprising a micro-order network structure is provided. The cell tissue produced according to the embodiment (3) is used, for example, for supplementing the function of a tissue or an organ by being transplanted into a living body. In addition, the cell tissue produced according to the embodiment (3) is used as a test cell tissue replacing an animal experiment or a clinical test.

Examples of the parenchymal organ include liver, pancreas, kidney, spleen, heart, lung, mammary gland tissue, adipose tissue, ovary, testis, and thymus, and examples of the cells forming a parenchymal organ include parenchymal cells forming those organs, epithelial cells, glandular cells, adipocytes, and stem cells or progenitor cells of these cells. The cells forming a parenchymal organ may be used alone or in combination of two or more thereof. Examples of combinations of two or more types of cells forming a parenchymal organ include hepatocytes and bile duct epithelial cells; pancreatic α cells, pancreatic β cells, and pancreatic δ cells; type I alveolar epithelial cells and type II alveolar epithelial cells; and mammary alveolar cells and mammary ductal epithelial cells.

The cells forming a parenchymal organ also include pluripotent stem cells. Pluripotent stem cells are undifferentiated cells having "self-renewal ability" capable of growing while maintaining an undifferentiated state and "pluripotency" capable of differentiating into all three germ layer series. Examples of pluripotent stem cells include embryonic stem cells (ES cells), induced pluripotent stem cells (iPS cells), embryonic germ cells (EG cells), embryonal carcinoma cells (EC cells), multipotent adult progenitor cells (MAP cells), an adult pluripotent stem cells (APS cells), and Muse cells (multi-lineage differentiating stress enduring cells). In the culturing step, a differentiation-inducing factor which induces differentiation into somatic cells of interest is added to a medium to differentiate pluripotent stem cells into somatic cells.

Embodiment (4)

A Culturing Step of Co-Culturing Cells Capable of Serving as a Feeder, Cells Forming a Parenchymal Organ, and at Least One of Vascular Endothelial Cells or Lymphatic Endothelial Cells According to the embodiment (4), a cell tissue comprising a network structure of vascular endothelial cells or lymphatic endothelial cells is provided on the surface or inside of the cell tissue of the parenchymal organ. The cell tissue produced according to the embodiment (4) is used, for example, for supplementing the function of a tissue or an organ by being transplanted into a living body. In addition, the cell tissue produced according to the embodiment (4) is used as a test cell tissue replacing an animal experiment or a clinical test.

The culturing step of the embodiment (4) may be a culturing step in which three types of cells are seeded at the same time and the three types of cells are simultaneously co-cultured or may be a culturing step in which three types of cells are seeded stepwise and the three types of cells are co-cultured stepwise. As the latter, for example, cells capable of serving as a feeder and at least one of vascular endothelial cells or lymphatic endothelial cells are seeded at the same time and cultured for several days to form a network structure of vascular endothelial cells or lymphatic endothelial cells, cells forming a parenchymal organ are then seeded, and culture is continued.

The culturing step is carried out, for example, by placing the porous film in a culture vessel with the side on which a plurality of opening pores are opened facing upward, seeding a cell suspension on the porous film, and culturing the cells under the culture conditions adapted to the seeded cell type. The culture vessel on which the porous film is placed may be any culture vessel known for cell culture. Examples of the material of the culture vessel include a resin (for example, polystyrene, polycarbonate, polyester, or acrylonitrile-butadiene-styrene resin), glass, ceramics, and metal. Examples of the shape of the culture vessel include a multi-well plate, a Petri dish, a microarray plate, a tube, a flask, a roller bottle, and a bag.

The present embodiment preferably includes, prior to the culturing step, a centrifugation step of seeding the cells on the surface of the porous film on the side where the plurality of opening pores are opened, and then applying a centrifugal force in the direction from the surface seeded with the cells to the opposite surface to move the cells to the inside of the plurality of opening pores. Since the cells seeded on the porous film migrate into the opening pores of the porous film by the centrifugation step, the proportion of the cells cultured in the pores increases.

In order to facilitate the centrifugation step in the case where the centrifugation step is included in the present embodiment, it is preferable to seed a cell suspension in which the cells are suspended in a relatively small amount of medium and carry out the centrifugation step. Then, the medium is added into the culture vessel after the centrifugation step.

[Medium and Culture Conditions]

The medium used in the present embodiment is selected from known media used for culturing mammalian cells according to the type of cells to be cultured. A specific example of the medium may be, for example, a medium optimized for the cell type by adding a cell growth factor to a basic medium such as Dulbecco's Modified Eagle's Medium (DMEM), DMEM: F-12 (Dulbecco's Modified Eagle Medium: Nutrient Mixture F-12), Eagle's minimal essential medium (EMEM), Minimum Essential Medium Alpha (MEMa), or Basal Medium Eagle (BME). Such a medium is commercially available. The medium used in the present embodiment may be a medium in which a plurality of media are mixed, depending on the type of cells to be co-cultured. The pH of the medium is, for example, pH 7.0 to 8.0 and preferably pH 7.3 to 7.4.

Various ingredients commonly added, for example, cell growth factors such as fibroblast growth factor-2 (FGF-2), transforming growth factor-β (TGF-β), epidermal growth factor (EGF), and vascular endothelial growth factor (VEGF); vitamin or vitamin derivatives such as ascorbic acid and retinoic acid; sugar sources such as glucose; amino acids; inorganic salts such as sodium selenite and sodium chloride; proteins such as transferrin; hormones such as insulin; differentiation-inhibiting factor; differentiation-inducing factor; antioxidants such as 2-mercaptoethanol and dithiothreitol; and antibiotics such as penicillin and streptomycin, may be added to the medium. The ingredients may be supplemented to the medium during cell culture in order to keep the concentration thereof within the desired range throughout the culture period. From the viewpoint of suppressing incorporation of antigenic substances, infectious sources, and the like into cell tissues, it is preferred that the medium does not contain serum and serum substitutes.

In the culturing step in the present embodiment, it is preferable to exchange the medium as appropriate. The media used for the series of culturing steps may not have the same composition. Culturing may be continued while replacing the medium with a medium having a different composition depending on the cell type to be co-cultured.

In the case where cells capable of serving as a feeder (first cells) and vascular endothelial cells or lymphatic endothelial cells (second cells) are co-cultured, or in the case where cells capable of serving as a feeder (first cells) and cells forming a parenchymal organ (second cells) are co-cultured, the mixing ratio of first cells:second cells is, for example, 1:0.5 to 1:5 in terms of number of first cells:number of second cells, and preferably 1:1 to 1:3 in terms of number of first cells:number of second cells.

In the case where cells capable of serving as a feeder (first cells), vascular endothelial cells or lymphatic endothelial cells (second cells), and cells forming a parenchymal organ (third cells) are co-cultured, the mixing ratio of those three types of cells is, for example, 1:1 to 1:10 in terms of (number of first cells+number of second cells):number of third cells, and preferably 1:2 to 1:5 in terms of (number of first cells+number of second cells):number of third cells. The mixing ratio of first cells:second cells is preferably within the above range.

The seeding density of the cells with respect to the porous film is, for example, $1 \times 10^3$ cells/cm$^2$ to $1 \times 10^6$ cells/cm$^2$, and preferably $1 \times 10^4$ cells/cm$^2$ to $1 \times 10^6$ cells/cm$^2$. In the case where a plurality of types of cells are co-cultured, it is preferable to set the total seeding density of the cells within the above range.

General conditions may be applied to the culture conditions in the present embodiment. For example, culture in an incubator at 37° C. and 5% (v/v) $CO_2$ concentration is applied. The culture period is not particularly limited, and culturing is preferably carried out for a period of time during which the network structure of the cells is sufficiently developed.

EXAMPLES

Hereinafter, embodiments of the invention will be described in detail with reference to Examples. The embodiments of the invention should not be interpreted restrictively by the following Examples.

Hereinafter, "PET" means polyethylene terephthalate, "PMMA" means polymethyl methacrylate, "PDMS" means polydimethylsiloxane, "SEM" means a scanning electron microscope, and "FBS" means fetal bovine serum.

Hereinafter, the opening pores and the communicating pores of the porous film are collectively referred to as "pores".

<Production of Porous Film and Culture Device>
[Porous Film]

5 parts by mass of polylactic acid, 94.5 parts by mass of trichloromethane, and 0.5 parts by mass of a polyacrylamide-based amphiphilic polymer as an amphiphilic compound were mixed to prepare a coating liquid. The coating liquid was applied on a PET film (film thickness: 188 μm) to form a coating film on the PET film. Humidified air was allowed to flow over the entire surface of the coating film, and water droplets were formed on the coating film due to dew condensation. While continuing to supply the humidified air to grow the water droplets, the water droplets were made to enter the coating film. Polylactic acid was precipitated around the water droplets by evaporation of the solvent contained in the coating film while growing water droplets until the water droplets were closely in contact with one another with the amphiphilic compound film interposed therebetween in the coating film. Then, the supply of the humidified air was stopped, and the temperature of the atmosphere was raised to evaporate the water droplets so that the portions where the water droplets have entered the coating film were left as opening pores, whereby a porous film comprising a porous layer formed of polylactic acid having a plurality of opening pores arranged in a honeycomb shape and having a communicating structure and a PET film layer was obtained. By adjusting the film thickness of the coating film, the amount of water vapor contained in the humidified air, and the timing of evaporating the water droplets, the dimensions of the opening pores and the communicating pores in the porous layer were adjusted to obtain each of porous films shown in Table 1.

[Culture Device]

Figure 4:
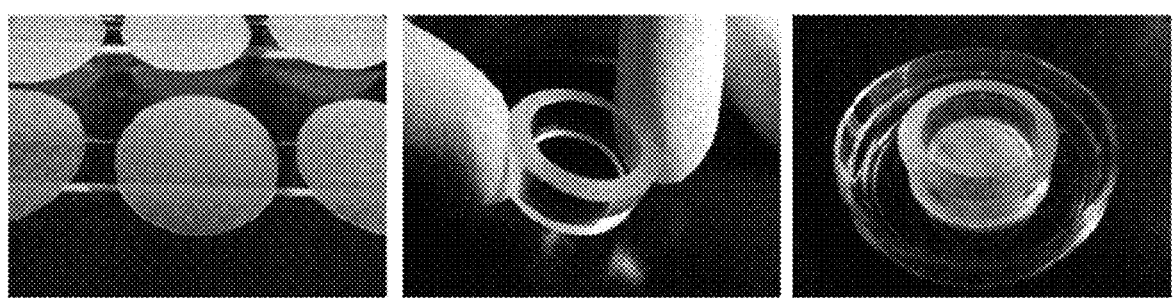
FIG. 4 shows components of a culture device and an example of the culture device.

The porous film was cut into a circle having a diameter of 23 mm, and a ring (outer diameter: 22 mm, inner diameter: 16 mm, height: 8 mm, made of PMMA, PDMS coated on the side) was attached to the outer periphery thereof using a double-sided adhesive tape (3M product number 1510, adhesive tape for skin) to prepare a ring-attached porous film. The ring-attached porous film was immersed in a 70% (v/v) ethanol aqueous solution for a few minutes for the purpose of sterilization and then washed with sterile water to remove ethanol. FIG. 4 shows an example of a porous film, a ring, and a culture device.

The ring-attached porous film was placed on a dish for tissue culture so that the PET film layer side of the porous film faced downward to obtain a culture device. For the purpose of sterilization, the culture device was irradiated with ultraviolet rays for 2 hours. The dimensions of the structure of the porous film of each culture device are shown in Table 1.

TABLE 1

| | Porous film | | | | | | | |
|---|---|---|---|---|---|---|---|---|
| Designation of culture device | Material | Arrangement of opening pores | Opening diameter | Variation coefficient of opening diameter | Center-to-center distance of openings | Depth of opening pore | Pore diameter of communicating pore | Variation coefficient of pore diameter of communicating pore |
| PLA40 | Polylactic acid | Honeycomb shape | 36 to 44 μm | 9% | 40 to 50 μm | 36 to 48 μm | 30 to 40 μm | 12% |
| PLA30 | Polylactic acid | Honeycomb shape | 27 to 33 μm | 7% | 30 to 39 μm | 27 to 36 μm | 22 to 30 μm | 9% |
| PLA20 | Polylactic acid | Honeycomb shape | 18 to 22 μm | 6% | 20 to 26 μm | 18 to 24 μm | 14 to 20 μm | 9% |
| PLA10 | Polylactic acid | Honeycomb shape | 9 to 11 μm | 4% | 10 to 14 μm | 10 to 12 μm | 7 to 10 μm | 7% |
| PLA3 | Polylactic acid | Honeycomb shape | 2 to 4 μm | 15% | 2.2 to 5 μm | 2 to 4.5 μm | 1.5 to 3.5 μm | 18% |

* All of the above have an arrangement in a honeycomb shape having a shape close to a regular hexagon as a unit.

Figure 5A:
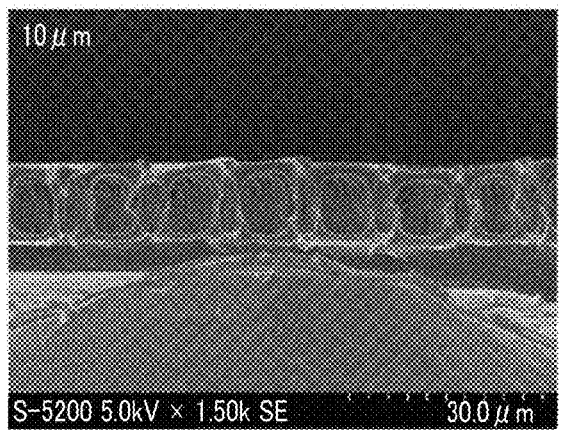
FIG. 5A is a scanning electron microscope image of a cross section and a surface of the porous film.
Figure 5A:
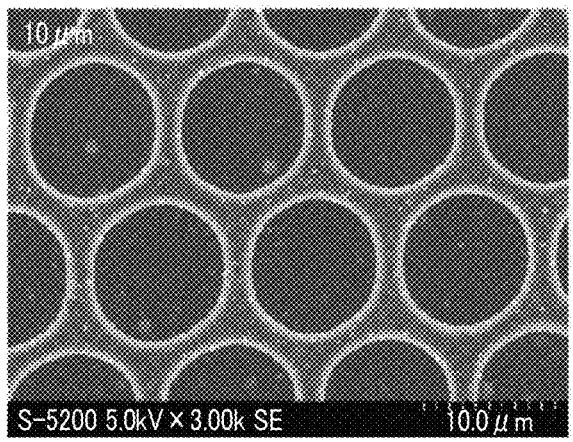
Figure 5B:
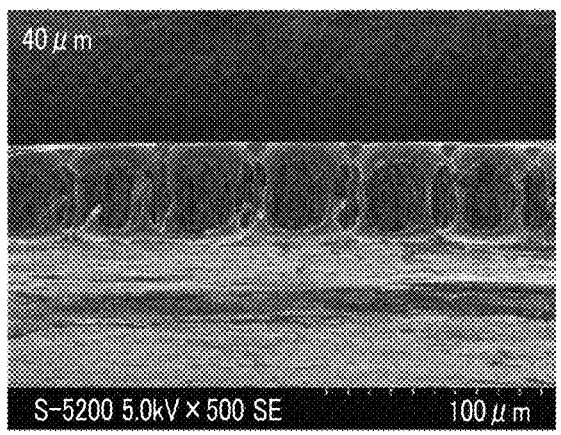
FIG. 5B is a scanning electron microscope image of the cross section and the surface of the porous film.
Figure 5B:
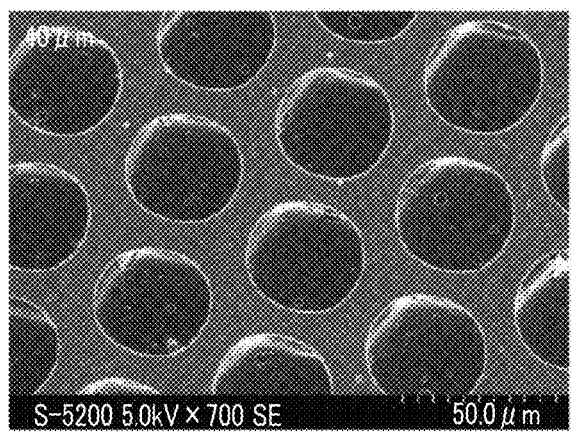

FIG. 5A is an SEM image of the cross section and the surface of the porous film comprised in PLA10, and FIG. 5B is a SEM image of the cross section and the surface of the porous film comprised in PLA40. In all of the porous films shown in Table 1, openings of adjacent opening pores were spaced apart by flat portions, and parts of individual wall surfaces were continuous and communicated with one another among the adjacent opening pores. In all of the porous films shown in Table 1, the opening pores arranged in the porous layer formed of polylactic acid did not penetrate the porous layer.

As control culture devices, a device (referred to as "Flat") comprising a laminate obtained by laminating an opening pore-free flat layer formed of polylactic acid on a PET film in place of a porous film, and a device (referred to as "TCP") with a ring attached to the culture surface of a dish for tissue culture (Tissue culture polystyrene: TCPS, diameter: 35 mm, trade name: Falcon Cell Culture Dish 353001, manufactured by Corning Incorporated) were prepared.

In these culture devices, the bottom surface inside the ring is the culture surface for culturing the cells, and the area of the bottom surface surrounded by the ring is 2 cm$^2$.

<Materials of Culture Experiment>

[Cells]

Mesenchymal stem cells: adult human bone marrow-derived normal cells, purchased from Lonza Japan Ltd. Hereinafter referred to as "MSCs".

Fibroblasts: human skin-derived normal cells NHSF46, distributed from the RIKEN Bioresource Center (3-1-1 Koyadai, Tsukuba, Ibaraki, Japan).

Vascular endothelial cells: human neonatal umbilical cord vein-derived normal cells, purchased from Lonza Japan Ltd. Hereinafter referred to as "HUVECs".

Liver-derived proliferating cells: human liver cancer-derived cells HepG2, distributed from the RIKEN BioResource Center (3-1-1 Koyadai, Tsukuba, Ibaraki, Japan).

[Culture Solution]

MSC medium: human mesenchymal stem cell medium kit MSCGM BulletKit, available from Lonza Japan Ltd.

NHSF 46 medium: MEMα+10% FBS

HUVEC medium: human endothelial cell medium kit EGM-2 BulletKit, available from Lonza Japan Ltd.

HepG2 medium: DMEM+10% FBS

Culture Experiment 1

Monoculture of Mesenchymal Stem Cells

MSCs were cultured alone under the following culture conditions using TCP, Flat, PLA3, PLA10, and PLA30 as culture devices.

Seeding density: $1\times10^5$ cells/disk ($5\times10^4$ cells/cm$^2$)

Centrifugation after seeding: culture devices comprising a porous film were subjected to centrifugation with a rotation radius of 120 mm, a rotation speed of 1100 rpm, and a rotation time of 3 minutes.

Osteogenic differentiation-inducing medium: hMSC differentiation BulletKit-osteogenic (product number: PT-3002, available from Lonza Japan Ltd.)

Adipogenic differentiation-inducing medium: hMSC differentiation BulletKit-adipogenic (product number: PT-3004, available from Lonza Japan Ltd.)

Culture solution volume: 1.0 ml/disk

Incubator: 37° C., 5% CO$_2$

Figure 6:
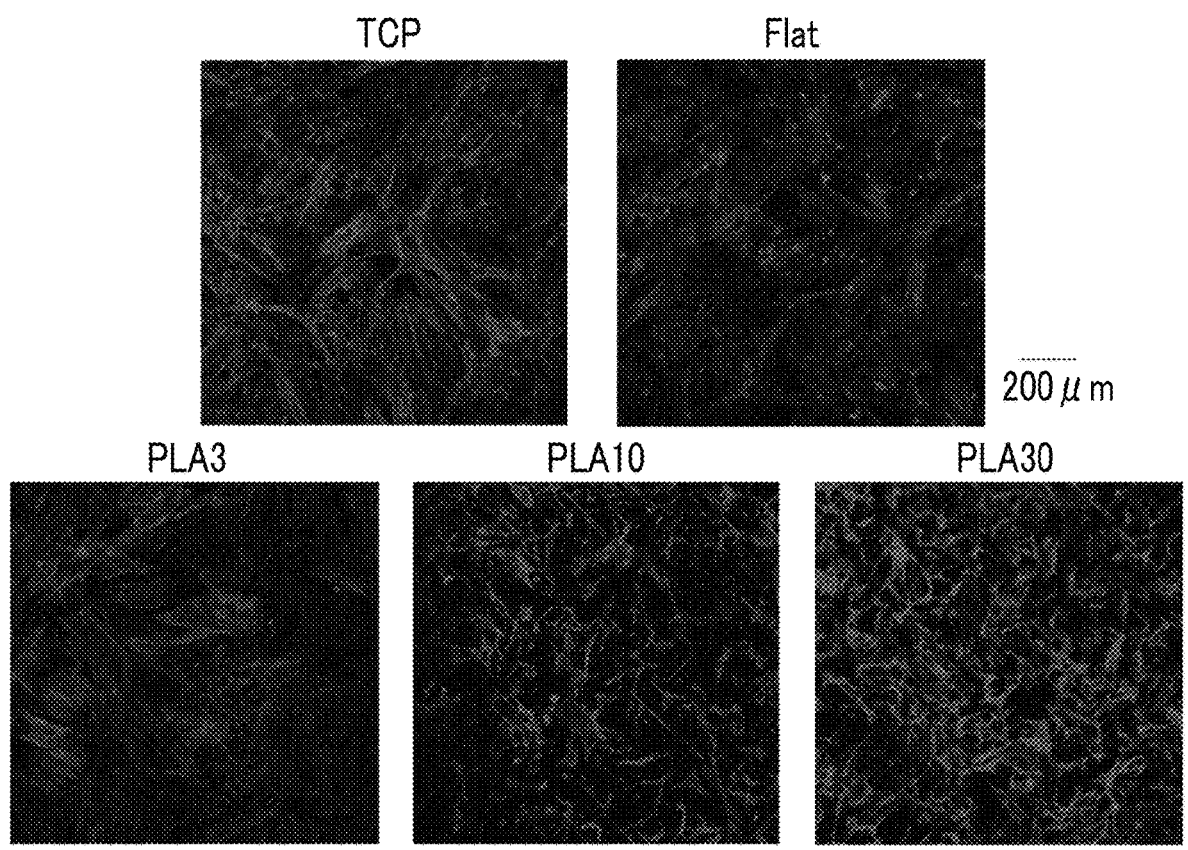
FIG. 6 is a fluorescent immunostaining image of actin in cells differentiated from mesenchymal stem cells.

The culture was started using the MSC medium. On Day 1 of culture, the medium was exchanged with a differentiation-inducing medium in which the osteogenic differentiation-inducing medium and the adipogenic differentiation-inducing medium were mixed in a ratio of 1:1. The differentiation-inducing medium was exchanged every 3 days, and the cells were cultured for a total of 15 days. On Day 14 of induction of differentiation, the expression of osteogenic differentiation markers Runx2 and Osx, and adipogenic differentiation markers C/EBPα and PPARγ was analyzed by real-time polymerase chain reaction (PCR). In addition, fluorescent immunostaining of actin was carried out on Day 14 of induction of differentiation. FIG. 6 shows a fluorescent immunostaining image of actin on Day 14 of induction of differentiation.

From the present experiment, the following has become clear.

Cell morphology changed depending on the size of the opening pore of the porous film. In PLA10 and PLA30, the cells showed an elongated morphology within the pores of the porous film. In TCP, Flat, and PLA3, the cells showed an extended morphology on the surface of the porous film.

The proliferation of cells in PLA3 and PLA10 was comparable to that of Flat, but the proliferation of cells in PLA30 was lower than that of Flat. This suggested that the proliferation of cells was inhibited in the case where the cells entered the pores of the porous film.

The results of real-time PCR analysis showed that differentiation into osteocytes and differentiation into adipocytes occurred in any culture device.

Culture Experiment 2

Co-Culture of Mesenchymal Stem Cells and Vascular Endothelial Cells

Under the following culture conditions using TCP and PLA40 as culture devices, HUVECs were cultured alone, or MSCs and HUVECs were co-cultured.

Monoculture: HUVECs seeding density of $1\times10^5$ cells/disk ($5\times10^4$ cells/cm$^2$). Culture in a mixed medium of MSC medium and HUVEC medium (MSC medium: HUVEC medium=1:2 by volume ratio).

Co-culture: MSCs and HUVECs were mixed and then seeded. MSCs seeding density of $0.5\times10^5$ cells/disk, HUVECs seeding density of $1\times10^5$ cells/disk, and total seeding density of $1.5\times10^5$ cells/disk ($7.5\times10^4$ cells/cm$^2$). Culture in a mixed medium of MSC medium and HUVEC medium (MSC medium:HUVEC medium=1:2 by volume ratio).

Centrifugation after seeding: half of the culture devices comprising a porous film were subjected to centrifugation with a rotation radius of 120 mm, a rotation speed of 1100 rpm, and a rotation time of 3 minutes.

Culture solution volume: 1.0 ml/disk

Incubator: 37° C., 5% CO$_2$

Culture period: cultured for 7 days. The medium was exchanged every 2 days.

Fluorescent immunostaining of HUVEC-specific cell surface marker CD31 was carried out on Days 3 and 7 of culture and observation was carried out using a confocal laser microscope system (Nikon C2$^+$, 10× objective lens). Focusing on the depth at which the network structure is most developed in the cell tissue, any 10 regions of 1.27 mm×1.27 mm (=1.61 mm$^2$) were selected to acquire a fluorescence image thereof, and the acquired fluorescence image was binarized using an image analysis software (Nikon NIS-Elements Basic Research). The major axes of the fluorescent regions scattered throughout the binarized image were individually measured and the lengths were summed up. Then, the total of the 10 regions was calculated and the calculated value was taken as the total length of the network formed by HUVECs. The areas of the fluorescent regions scattered throughout the binarized image were individually measured and the areas were summed up. Then, the total of the 10 regions was calculated and the calculated value was taken as the total area of the network formed by HUVECs.

Figure 7B:
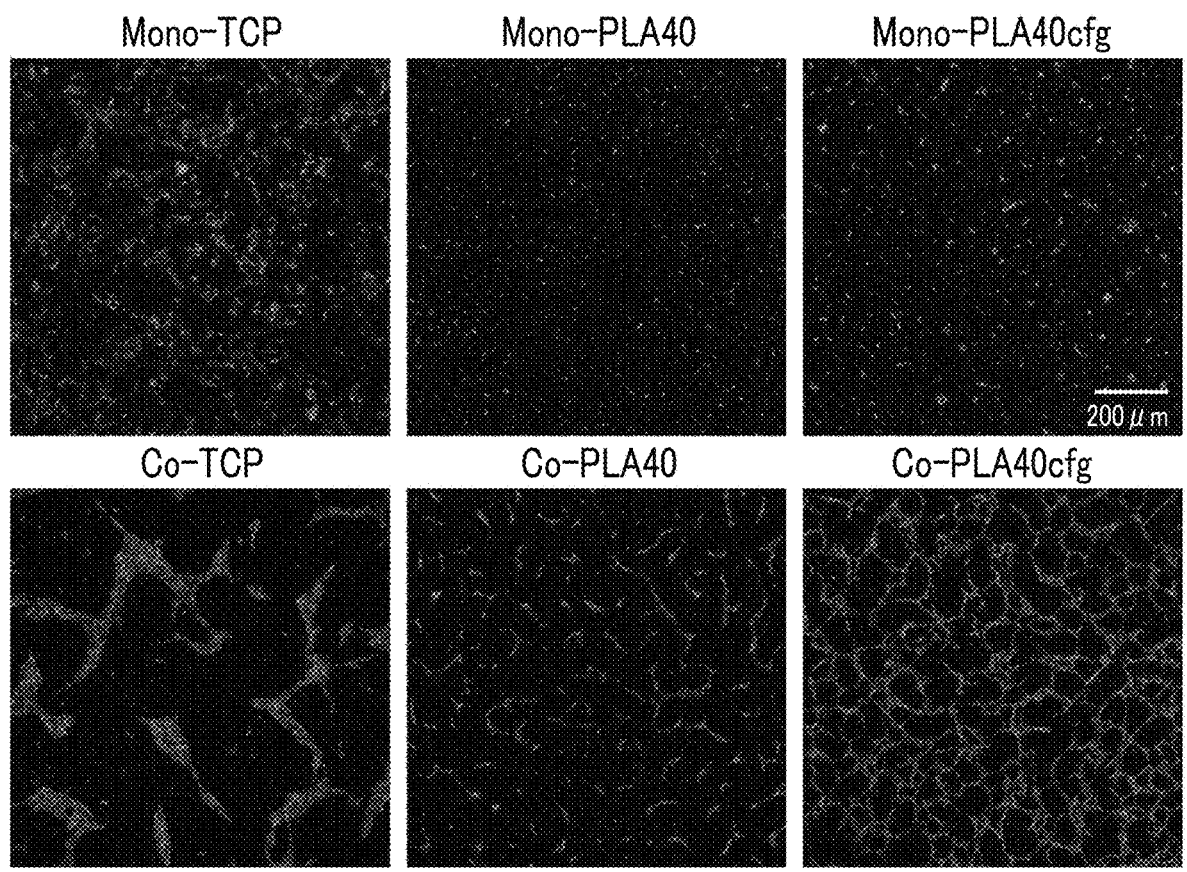
FIG. 7B is a fluorescent immunostaining image (high magnification) of CD31 in cells on Day 3 of culture in the same manner.
Figure 7C:
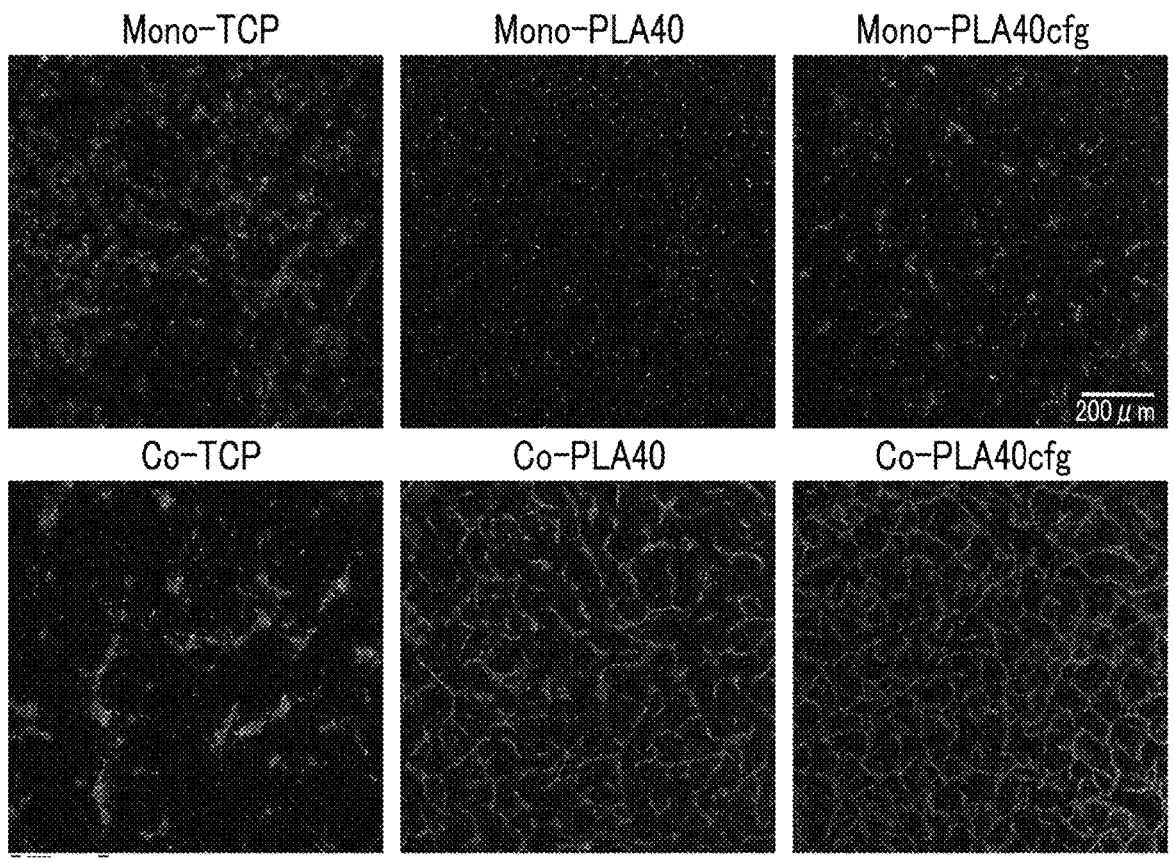
FIG. 7C is a fluorescent immunostaining image (high magnification) of CD31 in cells on Day 7 of culture in the same manner.

The analysis results of confocal laser microscope images and networks are shown in FIGS. 7A to 7D and Table 2. In FIGS. 7A to 7C, "Mono-" means monoculture and "Co-" means co-culture. In FIGS. 7A to 7D, an image attached with "cfg" is a culture example subjected to centrifugation, and an image without "cfg" is a culture example subjected to no centrifugation.

FIG. 7A: Fluorescent immunostaining image (low magnification) of CD31 on Day 3 of culture.

FIG. 7B: Fluorescent immunostaining image (high magnification) of CD31 on Day 3 of culture.

FIG. 7C: Fluorescent immunostaining image (high magnification) of CD31 on Day 7 of culture.

Figure 7D:
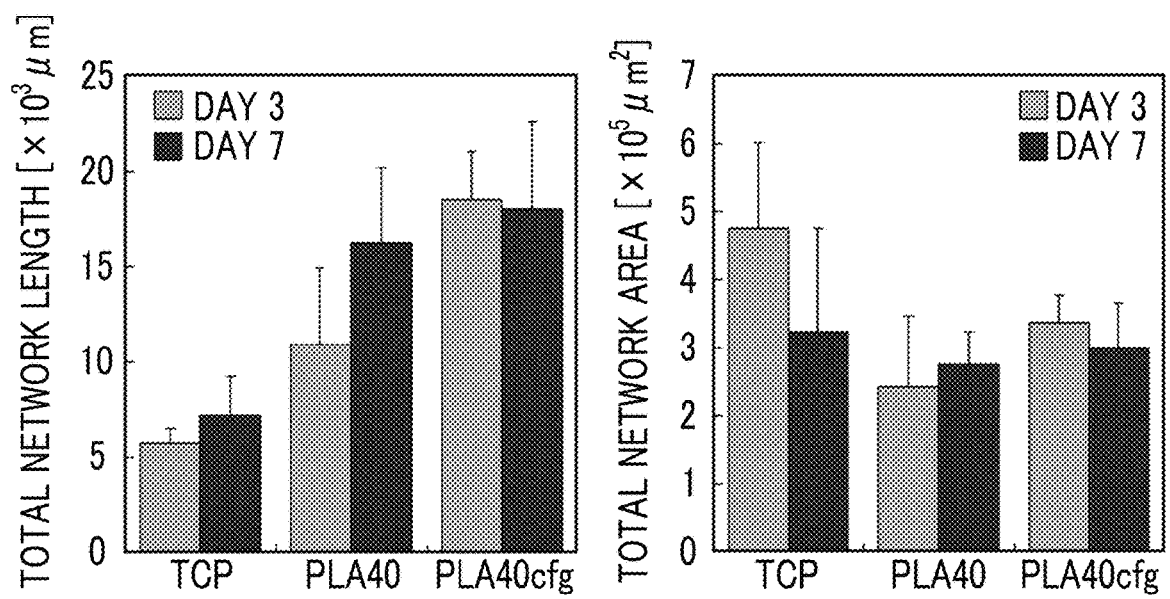
FIG. 7D is a graph showing network total length and total area in co-culture of mesenchymal stem cells and vascular endothelial cells.

FIG. 7D and Table 2: Total length and total area of the network in co-culture.

TABLE 2

| HUVECs/MSCs | | Total length of network [×$10^3$ μm] | Total area of network [×$10^5$ μm$^2$] |
|---|---|---|---|
| TCP | Day 3 of culture | 5.6 ± 0.8 | 4.7 ± 1.3 |
| | Day 7 of culture | 7.2 ± 2.0 | 3.3 ± 1.5 |
| PLA40 (without centrifugation) | Day 3 of culture | 10.9 ± 4.1 | 2.4 ± 1.1 |
| | Day 7 of culture | 16.3 ± 3.9 | 2.7 ± 0.5 |
| PLA40 (with centrifugation) | Day 3 of culture | 18.4 ± 2.6 | 3.4 ± 0.4 |
| | Day 7 of culture | 18.0 ± 4.6 | 3.0 ± 0.7 |

From the present experiment, the following has become clear.

The formation of capillary network-like network was difficult with only HUVECs which are cells forming the intima of blood vessels, but a capillary network-like network was formed by co-culture of MSCs and HUVECs. It was thought that cells supporting endothelial cells are required for the endothelial cells to form luminal structures, and MSCs secrete cytokines acting on endothelial cells and are capable of differentiation into parietal cells, so it was suggested that MSCs effectively acts on capillary network-like network formation of HUVECs.

The capillary network-like network formation progressed with time, and a more developed network was formed on Day 7 of culture as compared with Day 3 of culture.

In PLA40, many cells were present in the pores of the porous film. A developed capillary network-like network was formed in PLA40 as compared with TCP.

In PLA40 subjected to centrifugation, the capillary network-like network developed longer than in PLA40 subjected to no centrifugation. It was suggested that the centrifugation leads to an increase in the proportion of cells migrating into the pores of the porous film.

In the culture after the usual seeding operation, the cell density tended to be higher around the ring of the culture device, but in the culture after being subjected to centrifugation, relatively uniform network formation was observed in the entire culture surface. It was suggested that migration of the cells around the ring was suppressed due to migration of the seeded cells into the pores of the porous film by the centrifugation.

Culture Experiment 3

Co-Culture of Mesenchymal Stem Cells or Fibroblasts and Vascular Endothelial Cells Under the following culture conditions using TCP, Flat, and PLA40 as culture devices, MSCs and HUVECs were co-cultured, or NHSF46 and HUVECs were co-cultured.

Co-culture of MSCs and HUVECs: MSCs and HUVECs were mixed and then seeded. MSCs seeding density of 0.5×$10^5$ cells/disk, HUVECs seeding density of 1×$10^5$ cells/disk, and total seeding density of 1.5×$10^5$ cells/disk (7.5×$10^4$ cells/cm$^2$). Culture in a mixed medium of MSC medium and HUVEC medium (MSC medium: HUVEC medium=1:2 by volume ratio).

Co-culture of NHSF46 and HUVECs: NHSF46 and HUVECs were mixed and then seeded. NHSF46 seeding density of 0.5×$10^5$ cells/disk, HUVECs seeding density of 1×$10^5$ cells/disk, and total seeding density of 1.5×$10^5$ cells/disk (7.5×$10^4$ cells/cm$^2$). Culture in a mixed medium of NHSF46 medium and HUVEC medium (NHSF46 medium:HUVEC medium=1:2 by volume ratio).

Centrifugation after seeding: culture devices comprising a porous film were subjected to centrifugation with a rotation radius of 120 mm, a rotation speed of 1100 rpm, and a rotation time of 3 minutes.

Culture solution volume: 1.0 ml/disk

Incubator: 37° C., 5% $CO_2$

Culture period: cultured for 7 days. The medium was exchanged daily.

Fluorescent immunostaining of CD31 was carried out on Days 3 and 7 of culture and observation was carried out using a confocal laser microscope. The analysis results of the microscope image and the network are shown in FIGS. 8A to 8D and Table 3.

Figure 8A:
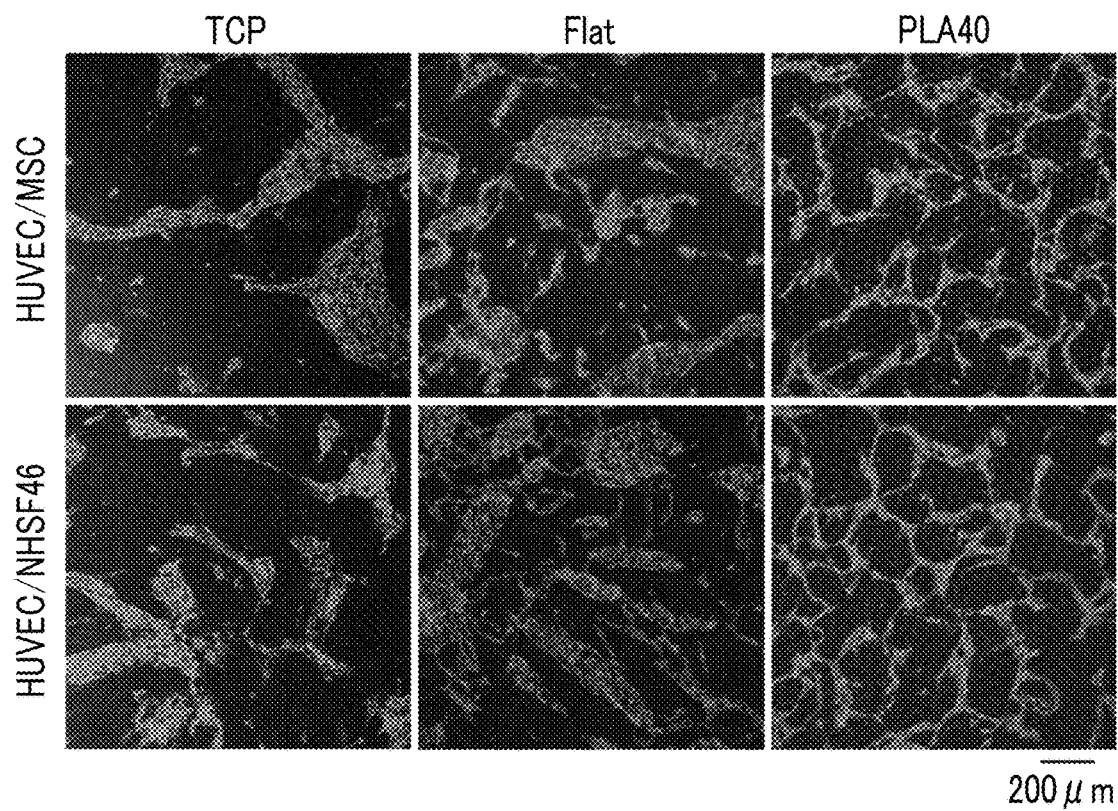
FIG. 8A is a fluorescent immunostaining image of CD31 in cells on Day 3 of culture in which mesenchymal stem cells or fibroblasts and vascular endothelial cells are co-cultured.

FIG. 8A: Fluorescent immunostaining image (high magnification) of CD31 on Day 3 of culture.

Figure 8B:
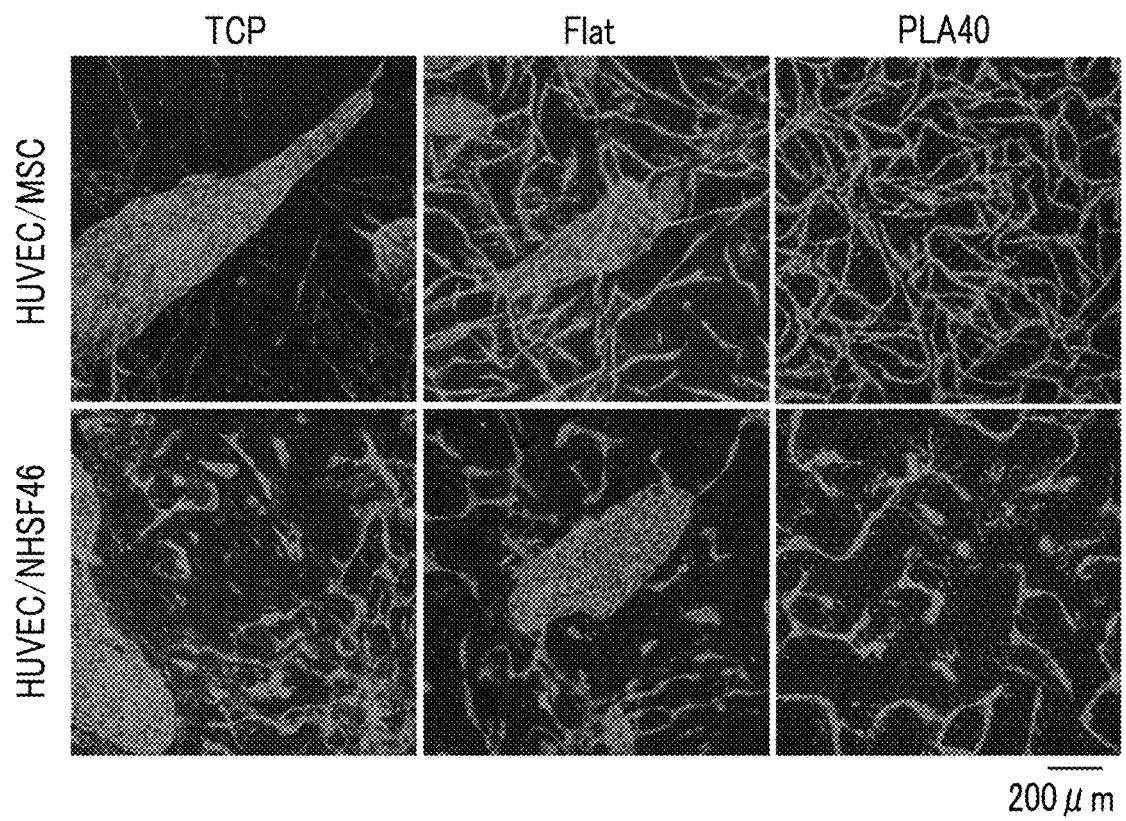
FIG. 8B is a fluorescent immunostaining image of CD31 in cells on Day 7 of culture in the same manner.
Figure 8C:
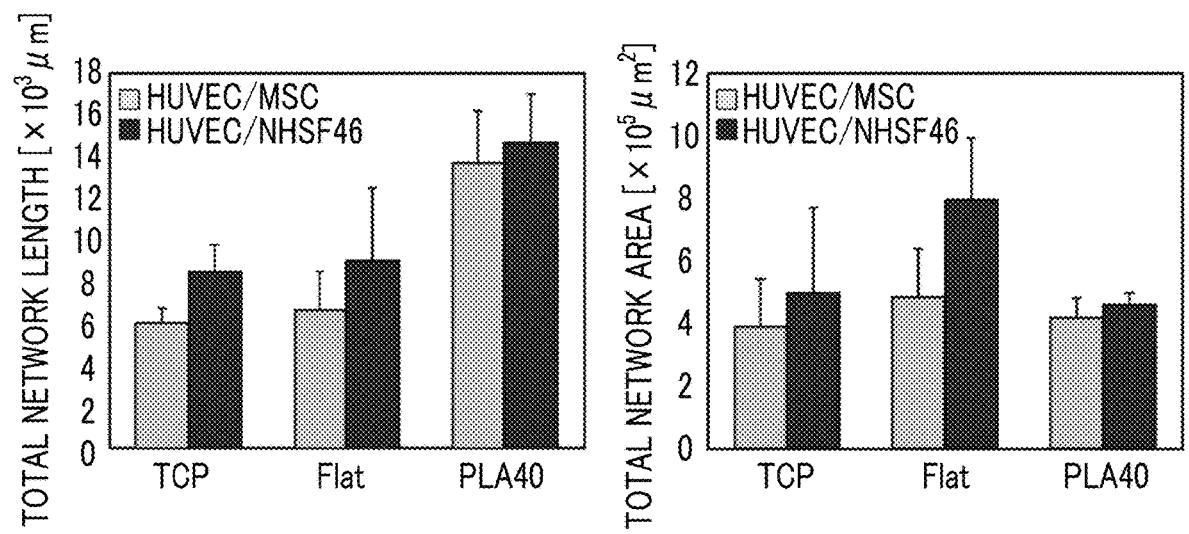
FIG. 8C is a graph showing the network total length and total area on Day 3 of culture.

FIG. 8B: Fluorescent immunostaining image (high magnification) of CD31 on Day 7 of culture FIG. 8C and Table 3: Total length and total area of the network on Day 3 of culture.

Figure 8D:
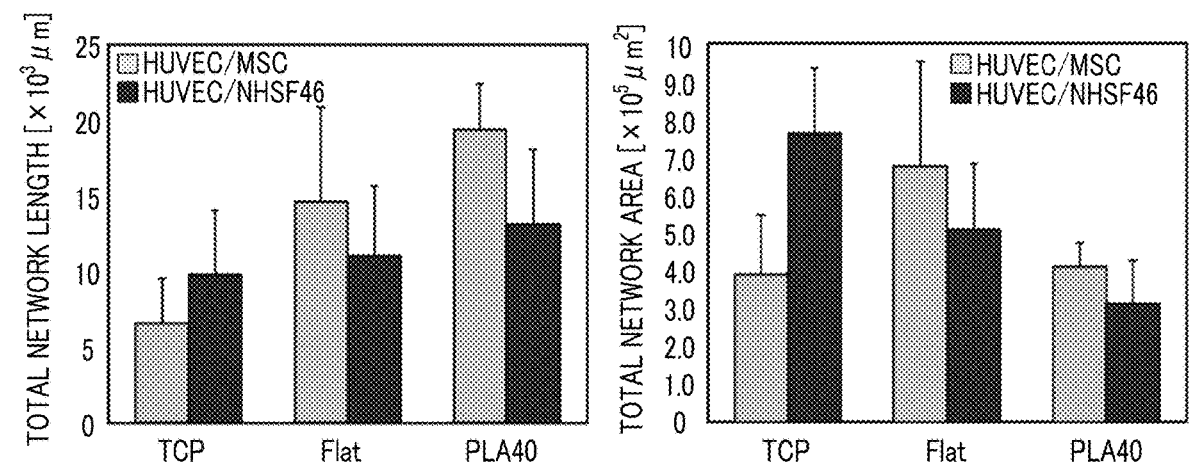
FIG. 8D is a graph showing the network total length and total area on Day 7 of culture.

FIG. 8D and Table 3: Total length and total area of the network on Day 7 of culture.

TABLE 3

| | | Total length of network [×$10^3$ μm] | Total area of network [×$10^5$ μm$^2$] |
|---|---|---|---|
| Day 3 of culture | | | |
| TCP | HUVECs/MSCs | 6.0 ± 0.7 | 3.9 ± 1.5 |
| | HUVECs/NHSF46 | 8.5 ± 1.3 | 5.0 ± 2.7 |
| Flat | HUVECs/MSCs | 6.6 ± 1.8 | 4.8 ± 1.6 |
| | HUVECs/NHSF46 | 9.0 ± 3.4 | 7.9 ± 2.0 |
| PLA40 | HUVECs/MSCs | 13.6 ± 2.5 | 4.2 ± 0.6 |
| | HUVECs/NHSF46 | 14.7 ± 2.3 | 4.6 ± 0.4 |
| Day 7 of culture | | | |
| TCP | HUVECs/MSCs | 6.6 ± 3.0 | 3.9 ± 1.6 |
| | HUVECs/NHSF46 | 9.8 ± 4.3 | 7.6 ± 1.7 |
| Flat | HUVECs/MSCs | 14.6 ± 6.2 | 6.7 ± 2.8 |
| | HUVECs/NHSF46 | 11.0 ± 4.7 | 5.1 ± 1.7 |
| PLA40 | HUVECs/MSCs | 19.4 ± 3.1 | 4.1 ± 0.6 |
| | HUVECs/NHSF46 | 13.1 ± 4.9 | 3.1 ± 1.1 |

From the present experiment, the following has become clear.

Co-culture of NHSF46 and HUVECs formed a capillary network-like network similar to the co-culture of MSCs and HUVECs.

The capillary network-like network developed with time.

A more developed network was formed in PLA40 as compared with TCP and Flat.

Culture Experiment 4

Examination of Dimensions of Porous Film

MSCs and HUVECs were co-cultured under the following culture conditions using TCP, Flat, PLA3, PLA10, PLA20, and PLA40 as culture devices.
  Seeding: MSCs and HUVECs were mixed and then seeded.
    Seeding density: MSCs: $0.5 \times 10^5$ cells/disk, HUVECs: $1 \times 10^5$ cells/disk, and total: $1.5 \times 10^5$ cells/disk ($7.5 \times 10^4$ cells/cm$^2$).
    Medium: a mixed medium of MSC medium and HUVEC medium, in which MSC medium:HUVEC medium=1:2 by volume ratio.
    Centrifugation after seeding: culture devices comprising a porous film were subjected to centrifugation with a rotation radius of 120 mm, a rotation speed of 1100 rpm, and a rotation time of 3 minutes.
  Culture solution volume: 1.0 ml/disk
  Incubator: 37° C., 5% $CO_2$
  Culture period: cultured for 7 days. The medium was exchanged every 2 days.

Figure 9A:
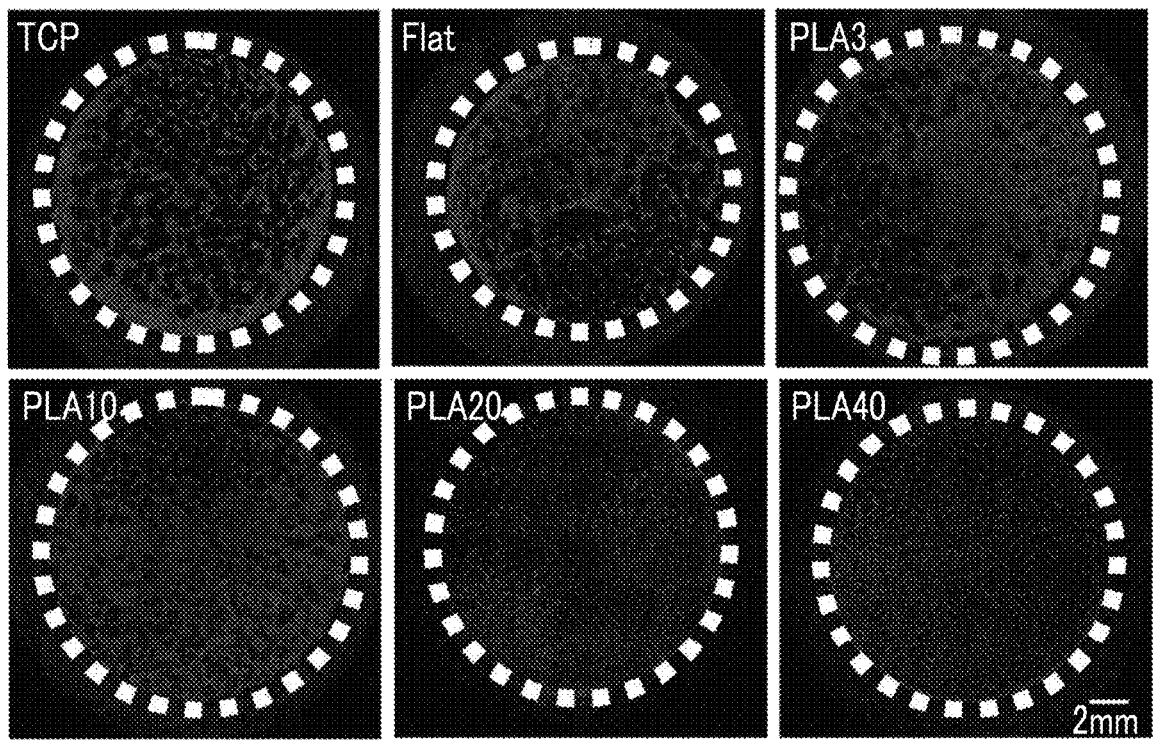
FIG. 9A is a fluorescent immunostaining image (low magnification) of CD31 in cells on Day 3 of culture in which mesenchymal stem cells and vascular endothelial cells are co-cultured using porous films having different opening pore sizes.
Figure 9B:
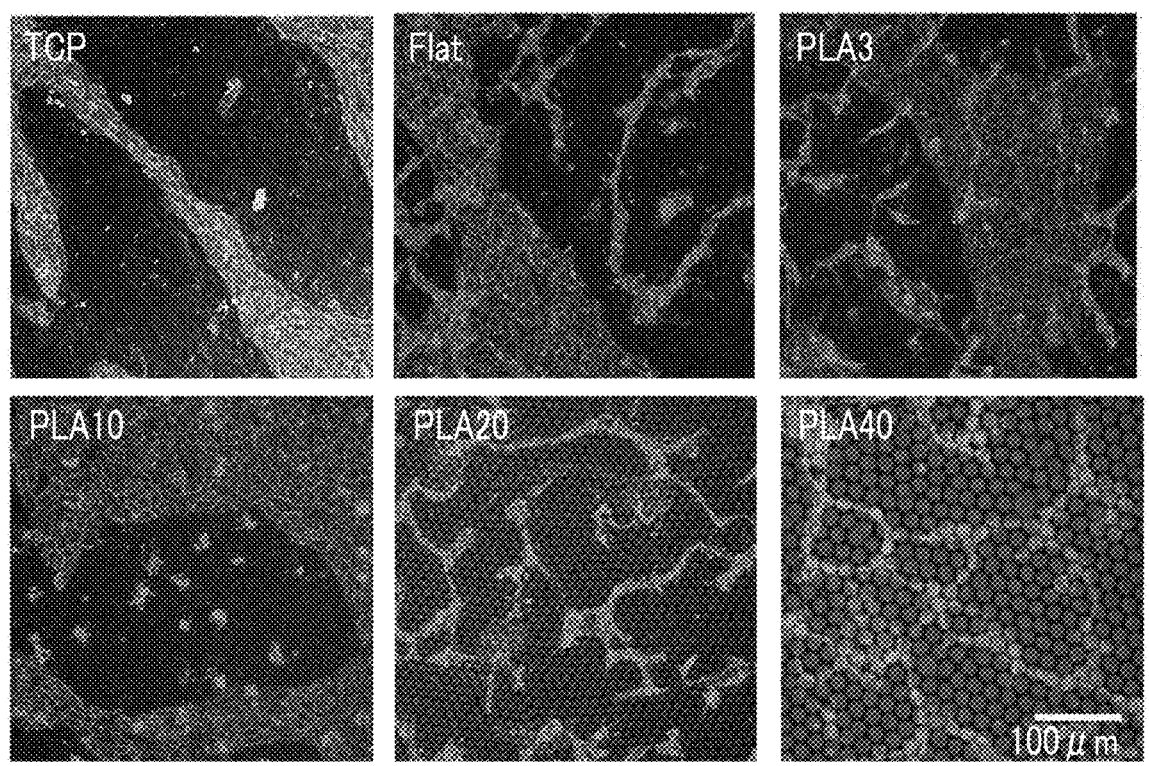
FIG. 9B is a fluorescent immunostaining image (high magnification) of CD31 in cells on Day 3 of culture in the same manner.
Figure 9C:
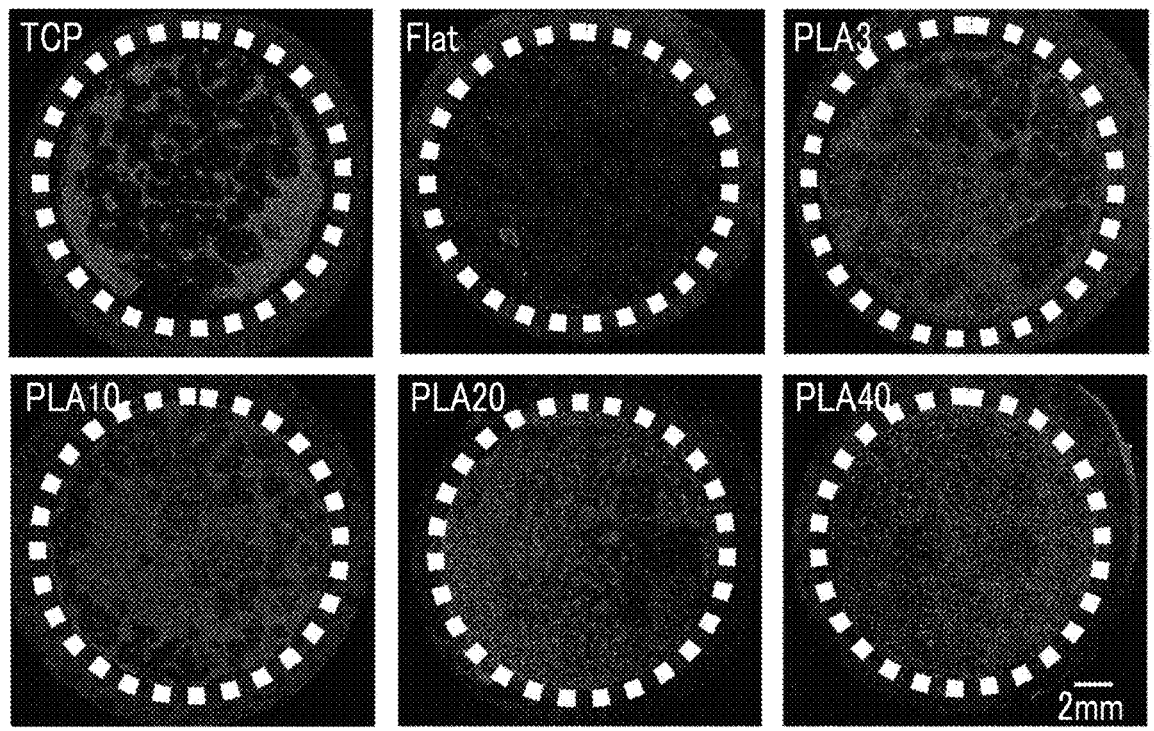
FIG. 9C is a fluorescent immunostaining image (low magnification) of CD31 in cells on Day 7 of culture in the same manner.
Figure 9D:
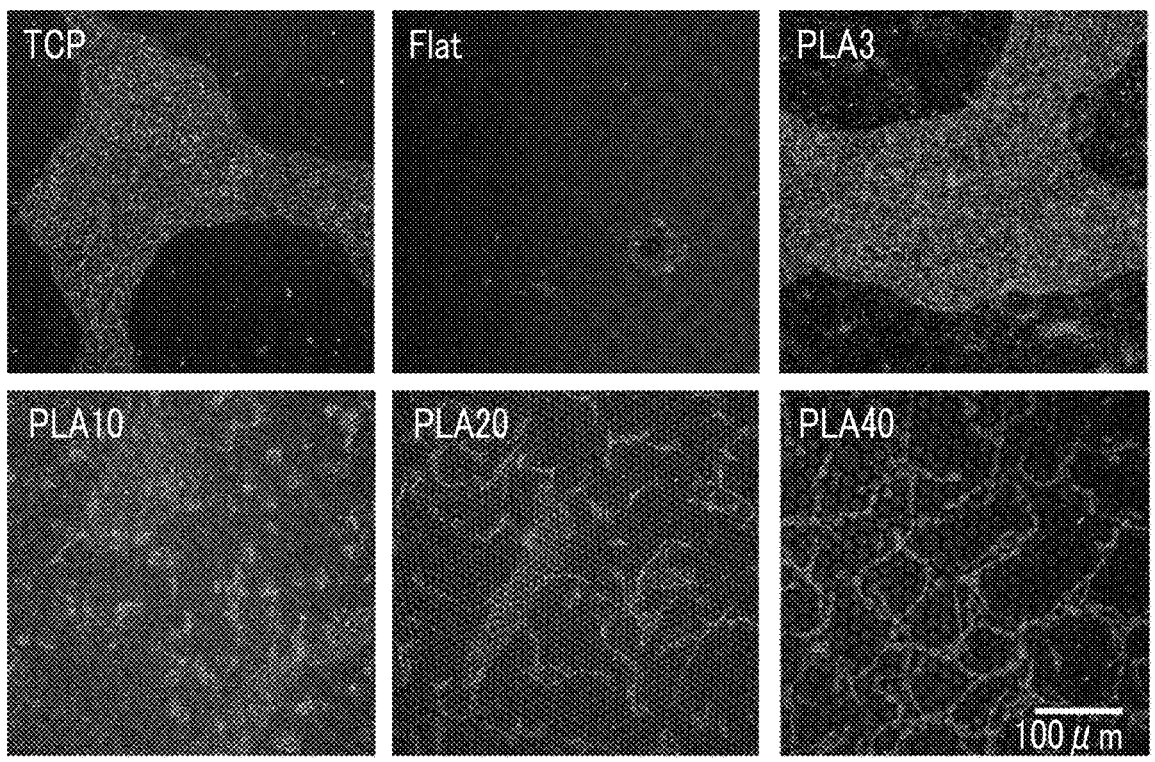
FIG. 9D is a fluorescent immunostaining image (high magnification) of CD31 in cells on Day 7 of culture in the same manner.
Figure 9E:
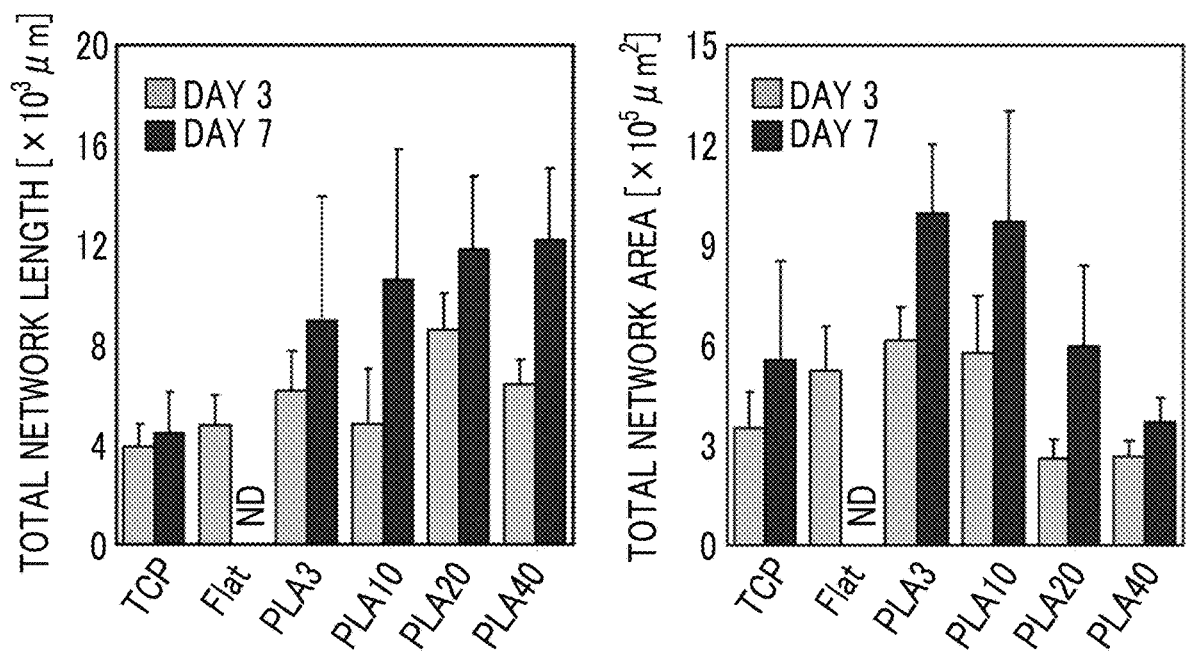
FIG. 9E is a graph showing the network total length and total area on Days 3 and 7 of culture.

Fluorescent immunostaining of CD31 was carried out on Days 3 and 7 of culture and observation was carried out using a confocal laser microscope. The analysis results of the microscope image and the network are shown in FIGS. 9A to 9E and Table 4.
  FIG. 9A: Fluorescent immunostaining image (low magnification) of CD31 on Day 3 of culture.
  FIG. 9B: Fluorescent immunostaining image (high magnification) of CD31 on Day 3 of culture.
  FIG. 9C: Fluorescent immunostaining image (low magnification) of CD31 on Day 7 of culture.
  FIG. 9D: Fluorescent immunostaining image (high magnification) of CD31 on Day 7 of culture.
  FIG. 9E and Table 4: Total length and total area of the network.

TABLE 4

| | | Total length of network [$\times 10^3$ μm] | Total area of network [$\times 10^5$ μm$^2$] |
|---|---|---|---|
| TCP | Day 3 of culture | 3.9 ± 0.9 | 3.6 ± 1.1 |
| | Day 7 of culture | 4.5 ± 1.6 | 5.6 ± 3.0 |
| Flat | Day 3 of culture | 4.8 ± 1.2 | 5.3 ± 1.3 |
| | Day 7 of culture | Not measurable due to peeling | Not measurable due to peeling |
| PLA3 | Day 3 of culture | 6.2 ± 1.6 | 6.1 ± 1.0 |
| | Day 7 of culture | 9.0 ± 5.0 | 9.9 ± 2.1 |
| PLA10 | Day 3 of culture | 4.9 ± 2.2 | 5.8 ± 1.7 |
| | Day 7 of culture | 10.6 ± 5.2 | 9.7 ± 3.4 |
| PLA20 | Day 3 of culture | 8.6 ± 1.5 | 2.6 ± 0.6 |
| | Day 7 of culture | 11.8 ± 3.0 | 6.0 ± 2.4 |
| PLA40 | Day 3 of culture | 6.4 ± 1.0 | 2.7 ± 0.5 |
| | Day 7 of culture | 12.2 ± 2.9 | 3.7 ± 0.7 |

From the present experiment, the following has become clear.
  In PLA3 and PLA10, the cells showed an extended morphology on the surface of the porous film and no formation of a network.
  In PLA20, the cells showed an extended morphology on the surface of the porous film and a form in which a network was formed within the pores of the porous film.
  In PLA40, a capillary network-like network was formed.
  As described above, the cell morphology changed depending on the size of the opening pores of the porous film. Since the major axis of the cell used in the present experiment was about 20 it was suggested that the cells were likely to form a network within the pores of the porous film, in the case where the size of the opening pore of the porous film was equal to or larger than the cell size.

Culture Experiment 5

Simultaneous Co-Culture of Three Types of Cells

MSCs, HUVECs, and HepG2 were co-cultured under the following culture conditions using TCP and PLA40 as culture devices.
  Seeding: MSCs, HUVECs, and HepG2 were mixed and then seeded. HepG2 was previously labeled with a fluorescent dye CellTracker Red.
    Seeding density: MSCs: $0.5 \times 10^5$ cells/disk, HUVECs: $1 \times 10^5$ cells/disk, and HepG2: $5 \times 10^5$ cells/disk.
    Medium: a mixed medium of MSC medium, HUVEC medium, and HepG2 medium, in which MSC medium:HUVEC medium:HepG2 medium=1:2:3 by volume ratio.
    Centrifugation after seeding: culture devices comprising a porous film were subjected to centrifugation with a rotation radius of 120 mm, a rotation speed of 1100 rpm, and a rotation time of 3 minutes.
  Culture solution volume: 1.0 ml/disk
  Incubator: 37° C., 5% $CO_2$
  Culture period: cultured for 3 days. The medium was exchanged daily.

Figure 10A:
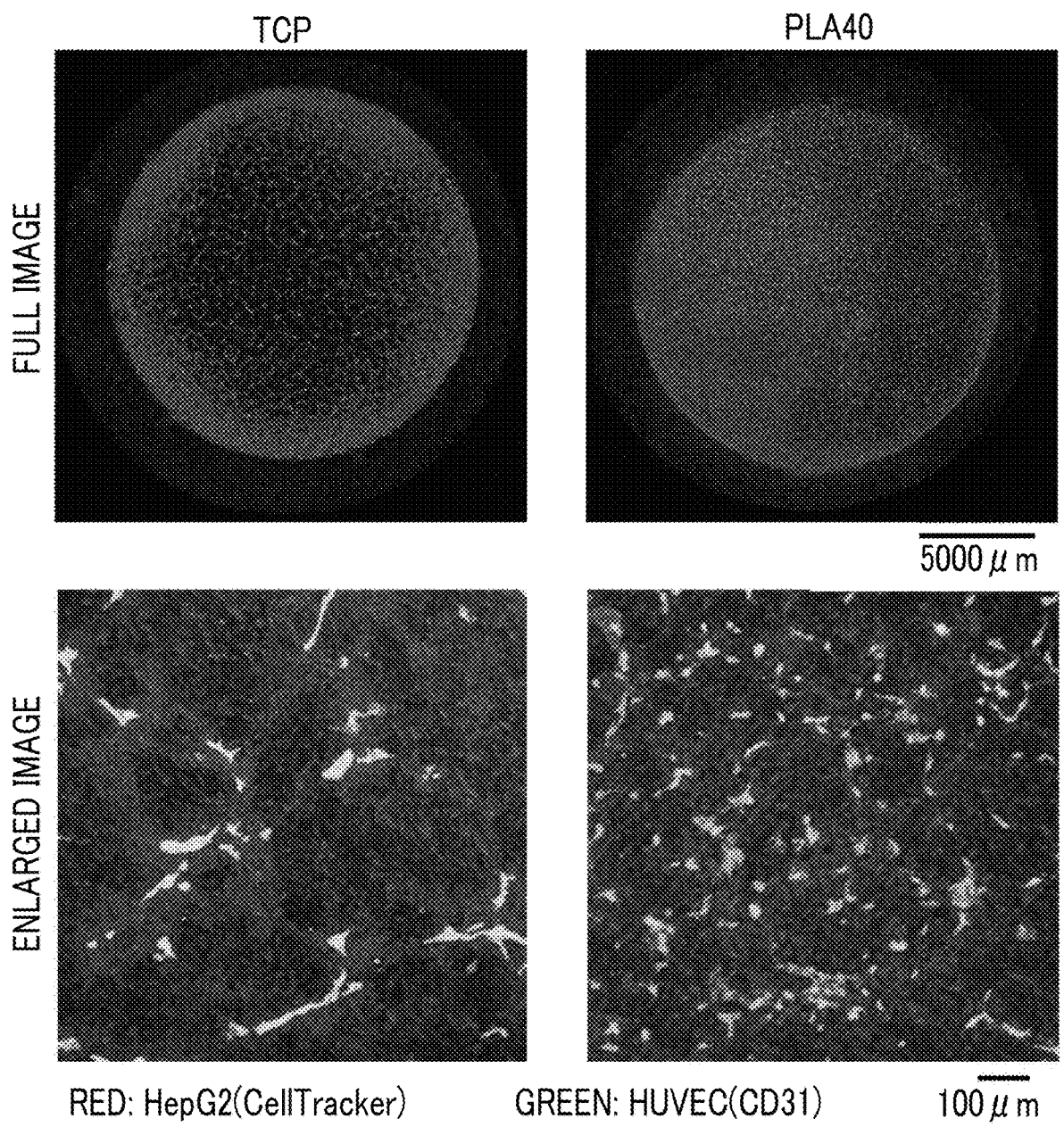
FIG. 10A is a fluorescence image on Day 3 of culture in which three types of cells are co-cultured at the same time.
Figure 10B:
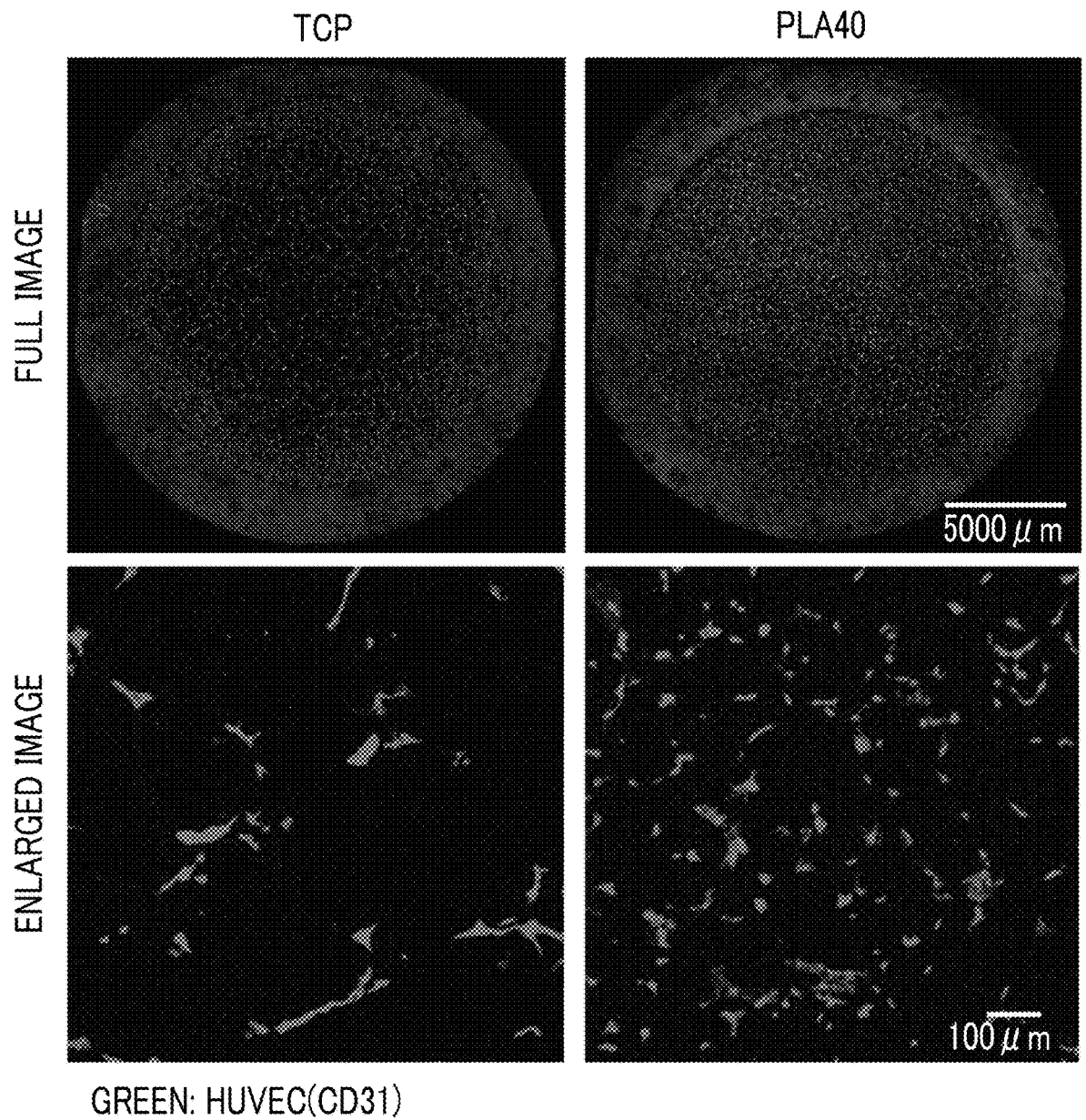
FIG. 10B is a fluorescent immunostaining image of CD31 in cells on Day 3 of culture in the same manner.

Fluorescent immunostaining of CD31 was carried out on Day 3 of culture and observation was carried out using a confocal laser microscope to analyze the network formed by the cells. FIGS. 10A to 10B show microscope images.
  FIG. 10A: Fluorescence image on Day 3 of culture (superimposed image of green fluorescence and red fluorescence).
  FIG. 10B: Fluorescent immunostaining image of CD31 on Day 3 of culture.

From the present experiment, the following has become clear.
  In PLA40, the cells formed a network structure, but the connection state between the networks was poor.
  The co-culture of three types of MSCs, HUVECs, and HepG2 had a higher seeding density as compared to the co-culture of two types of MSCs and HUVECs, and therefore the cell migration was reduced due to a high density of cells filled in the pores of the porous film, suggesting that network formation has been slowed or delayed. It was speculated that network formation could be achieved by optimizing the seeding density or prolonging the culture time.

Culture Experiment 6

Stepwise Co-Culture of Three Types of Cells

MSCs, HUVECs, and HepG2 were co-cultured under the following culture conditions using TCP and PLA40 as culture devices.

Seeding: MSCs and HUVECs were mixed, seeded, cultured for 3 days, and then HepG2 was seeded. HepG2 was previously labeled with a fluorescent dye Cell-Tracker Red.

Seeding density: MSCs: $0.5 \times 10^5$ cells/disk, HUVECs: $1 \times 10^5$ cells/disk, and HepG2 $5 \times 10^5$ cells/disk.

Centrifugation after seeding: culture devices comprising a porous film were subjected to centrifugation with a rotation radius of 120 mm, a rotation speed of 1100 rpm, and a rotation time of 3 minutes.

Culture solution volume: 1.0 ml/disk

Incubator: 37° C., 5% $CO_2$

Culture period: The co-culture of two types of cells was carried out for 3 days, and the co-culture of three types of cells was carried out for 3 days.

Medium: For 3 days from the start of culture, the cells were cultured in a mixed medium of MSC medium and HUVEC medium (1:2 by volume ratio), and medium exchange was carried out on Day 1. After seeding HepG2, the medium was exchanged to a mixed medium of MSC medium, HUVEC medium, and HepG2 medium (1:2:3 by volume ratio). The cells were cultured while exchanging the medium every day.

Figure 11A:
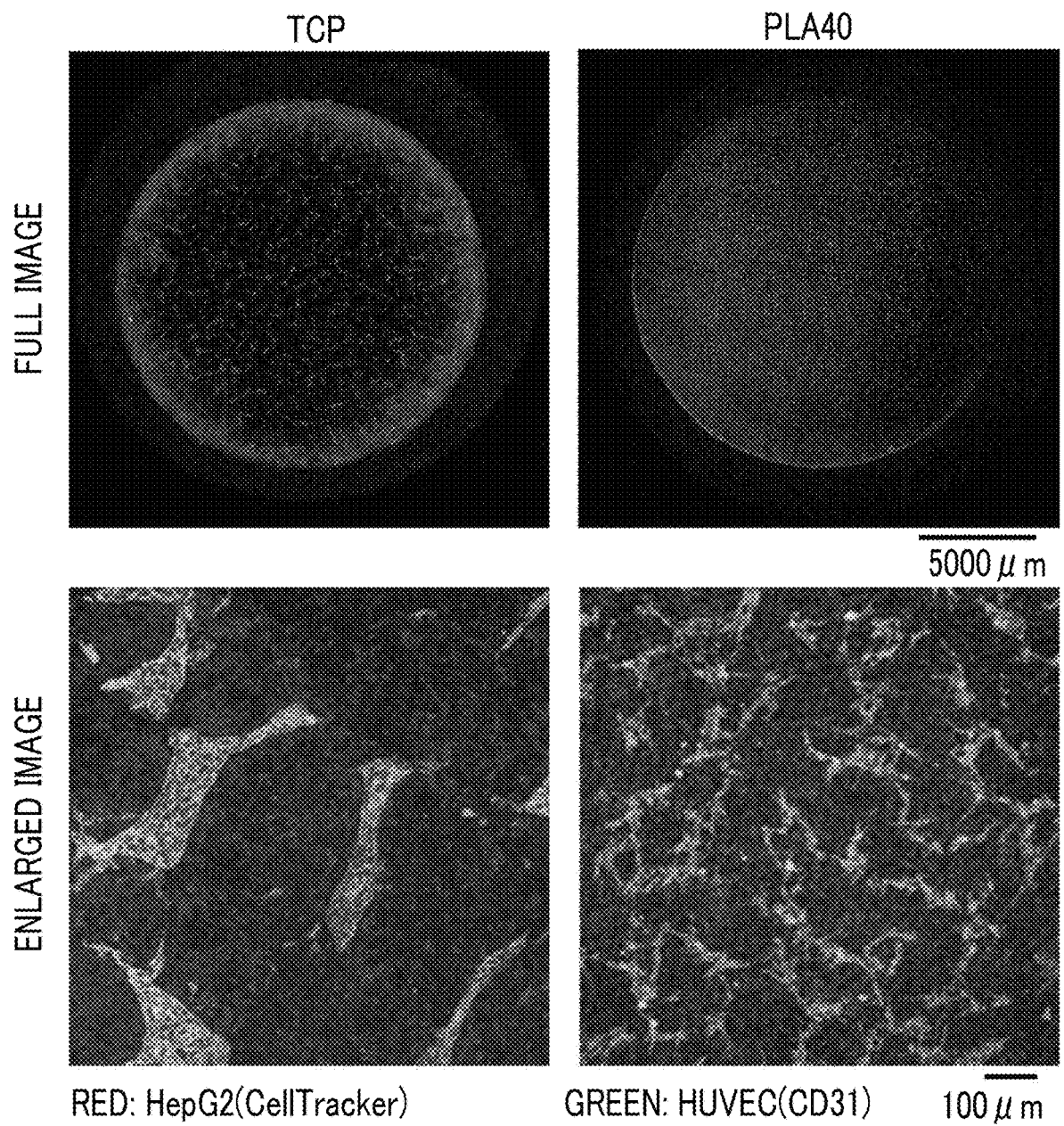
FIG. 11A is a fluorescence image on Day 3 of co-culture in which three types of cells are co-cultured stepwise.
Figure 11B:
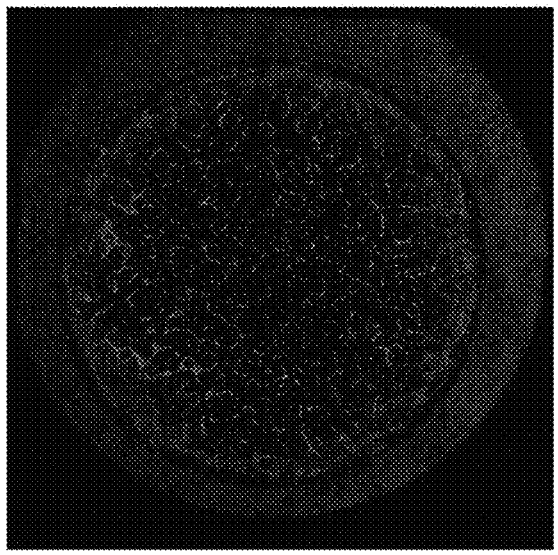
FIG. 11B is a fluorescent immunostaining image of CD31 in cells on Day 3 of co-culture in the same manner.
Figure 11B:
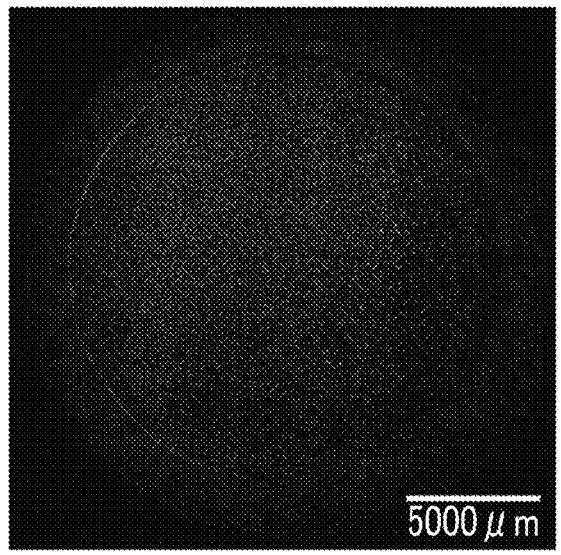
Figure 11B:
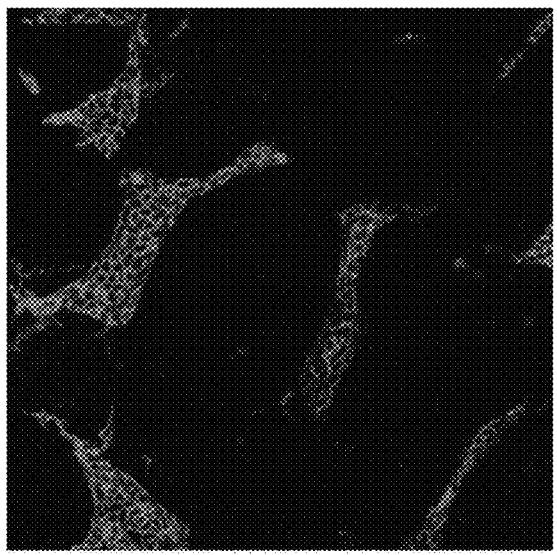
Figure 11B:
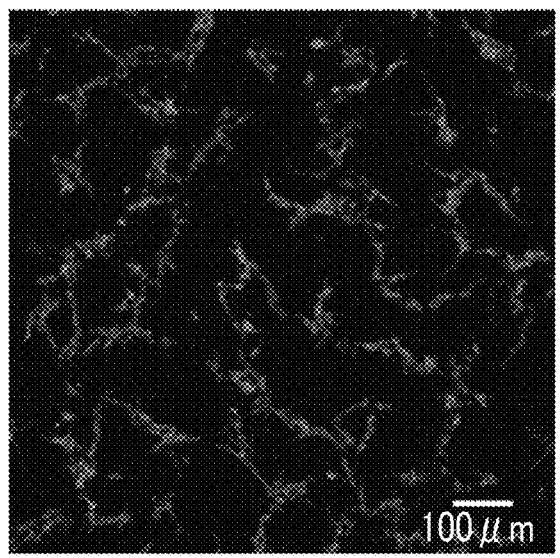
Figure 11C:
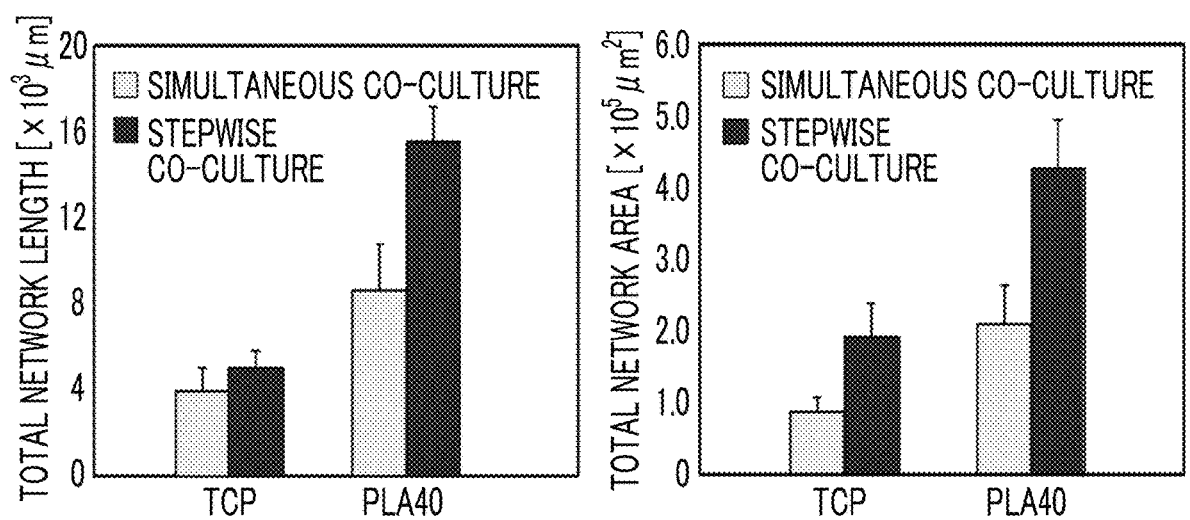
FIG. 11C is a graph showing the network total length and total area in each of simultaneous co-culture and stepwise co-culture on Day 3 of co-culture.

Fluorescent immunostaining of CD31 was carried out on Day 3 after seeding HepG2, and the network formed by the cells was analyzed from the fluorescence image of CD31 and the fluorescence image of HepG2. FIGS. 11A to 11B show microscope images. FIG. 11C and Table 5 show the total length and total area of the network obtained by analyzing the fluorescence image of CD31.

FIG. 11A: Fluorescence image on Day 3 of culture after seeding HepG2 (superimposed image of green fluorescence and red fluorescence).

FIG. 11B: Fluorescent immunostaining image of CD31 on Day 3 of culture after seeding HepG2.

FIG. 11C and Table 5: Total length and total area of the network in each of simultaneous co-culture (Culture Experiment 5) and stepwise co-culture (Culture Experiment 6) on Day 3 of co-culture of three types of cells.

TABLE 5

| | HepG2/HUVECs/MSCs | Total length of network [×10³ μm] | Total area of network [×10⁵ μm²] |
|---|---|---|---|
| TCP | Simultaneous co-culture | 4.0 ± 1.0 | 0.9 ± 0.2 |
| | Stepwise co-culture | 5.1 ± 0.8 | 1.9 ± 0.5 |
| PLA40 | Simultaneous co-culture | 8.6 ± 2.1 | 2.1 ± 0.5 |
| | Stepwise co-culture | 15.6 ± 1.6 | 4.3 ± 0.7 |

From the present experiment, the following has become clear.

A narrow and long network was formed in PLA40 as compared with TCP.

Stepwise co-culture had an increased network linkage as compared with simultaneous co-culture. It was suggested that seeding of HepG2 following co-culture of MSCs and HUVECs to pre-form a network is effective for the formation of a higher order network structure.

The disclosure of JP 2016-188627 filed on Sep. 27, 2016 is hereby incorporated by reference in its entirety.

All documents, patent applications, and technical standards described in the present specification are incorporated herein by reference to the same extent as the case where each individual document, patent application, and technical standard were specifically and individually indicated to be incorporated by reference.

What is claimed is:

1. A method for producing a cell tissue, comprising:
   a culturing step of co-culturing cells capable of serving as a feeder and at least one of vascular endothelial cells or lymphatic endothelial cells inside opening pores and communicating pores of a porous film having a plurality of the opening pores provided on a surface thereof and the communicating pores communicating mutually adjacent opening pores with one another, wherein
   the porous film is a monolayer of a porous layer comprising the opening pores and the communicating pores, or a laminate consisting of a monolayer of a porous layer disposed on a substrate, the porous layer comprising the opening pores and the communicating pores,
   an opening diameter of the opening pore is in a range of 18 μm to 44 μm,
   a depth of the opening pore is in a range of 18 μm to 48 μm,
   a pore diameter of the communicating pore is in a range of 14 μm to 40 μm, and
   the plurality of opening pores, which have an isotropic shape and the same size in the plane direction, are arranged in a honeycomb shape on the surface of the porous film.

2. The method for producing a cell tissue according to claim 1, wherein the culturing step is a culturing step of co-culturing the cells capable of serving as a feeder and cells forming a parenchymal organ inside the opening pores and the communicating pores.

3. The method for producing a cell tissue according to claim 1, wherein the culturing step is a culturing step of co-culturing the cells capable of serving as a feeder, cells forming a parenchymal organ, and at least one of vascular endothelial cells or lymphatic endothelial cells inside the opening pores and the communicating pores.

4. The method for producing a cell tissue according to claim 1, wherein the cells capable of serving as a feeder are at least one of mesenchymal stem cells or fibroblasts.

5. The method for producing a cell tissue according to claim 1, wherein the communicating pores are provided at substantially the same depth over an entire area of the porous film in a plane direction.

6. The method for producing a cell tissue according to claim 1, wherein a pore diameter of the communicating pore is in a range of 50% to 500% of a major axis of the cell seeded on the porous film.

7. The method for producing a cell tissue according to claim 1, wherein a variation coefficient of a pore diameter of the communicating pore is 30% or less.

8. The method for producing a cell tissue according to claim 1, wherein a major axis of the opening pore in a plane direction of the porous film is in a range of 10 μm to 100 μm.

9. The method for producing a cell tissue according to claim 1, wherein a depth of the opening pore is in a range of 10 μm to 100 μm.

10. The method for producing a cell tissue according to claim 1, wherein a variation coefficient of an opening diameter of the opening pore is 20% or less.

11. The method for producing a cell tissue according to claim 1, further comprising:
    prior to the culturing step, a centrifugation step of seeding the cells on a surface of the porous film on a side where the plurality of opening pores are opened, and then applying a centrifugal force in a direction from a surface seeded with the cells to an opposite surface to move the cells to the inside of the plurality of opening pores.

12. A porous film comprising:

a plurality of opening pores provided on a surface thereof; and communicating pores communicating mutually adjacent opening pores with one another, wherein the porous film is a monolayer of a porous layer comprising the opening pores and the communicating pores, or a laminate consisting of a monolayer of a porous layer disposed on a substrate, the porous layer comprising the opening pores and the communicating pores, an opening diameter of the opening pore is in a range of 18 μm to 44 μm, a depth of the opening pore is in a range of 18 μm to 48 μm, a pore diameter of the communicating pore is in a range of 14 μm to 40 μm, a major axis of the opening pore in a plane direction of the porous film is in a range of 20 μm to 100 μm, and the plurality of opening pores, which have an isotropic shape and the same size in the plane direction, are arranged in a honeycomb shape on the surface of the porous film.

13. A porous film comprising: a plurality of opening pores provided on a surface thereof; and communicating pores communicating mutually adjacent opening pores with one another, wherein the porous film is a monolayer of a porous layer comprising the opening pores and the communicating pores, or a laminate consisting of a monolayer of a porous layer disposed on a substrate, the porous layer comprising the opening pores and the communicating pores, an opening diameter of the opening pore is in a range of 18 μm to 44 μm, a depth of the opening pore is in a range of 18 μm to 48 μm, a pore diameter of the communicating pore is in a range of 14 μm to 40 μm, a depth of the opening pore is in a range of 20 μm to 100 μm, and the plurality of opening pores, which have an isotropic shape and the same size in the plane direction, are arranged in a honeycomb shape on the surface of the porous film.

* * * * *